(12) United States Patent
Borrebaeck et al.

(10) Patent No.: US 10,048,265 B2
(45) Date of Patent: Aug. 14, 2018

(54) METHODS AND ARRAYS FOR USE IN THE SAME

(71) Applicant: IMMUNOVIA AB, Lund (SE)

(72) Inventors: Carl Arne Krister Borrebaeck, Lund (SE); Christer Lars Bertil Wingren, Sandby (SE)

(73) Assignee: Immunovia AB, Lund (SE)

( * ) Notice: Subject to any disclaimer, the term of this patent is extended or adjusted under 35 U.S.C. 154(b) by 77 days.

(21) Appl. No.: 14/781,839

(22) PCT Filed: Apr. 2, 2014

(86) PCT No.: PCT/EP2014/056630
§ 371 (c)(1),
(2) Date: Oct. 1, 2015

(87) PCT Pub. No.: WO2014/161910
PCT Pub. Date: Oct. 9, 2014

(65) Prior Publication Data
US 2016/0041173 A1    Feb. 11, 2016

(30) Foreign Application Priority Data

Apr. 2, 2013  (GB) .................. 1305940.7

(51) Int. Cl.
| | | |
|---|---|---|
| G01N 33/53 | (2006.01) | |
| G01N 33/574 | (2006.01) | |
| C07K 16/18 | (2006.01) | |
| C07K 16/22 | (2006.01) | |
| C07K 16/24 | (2006.01) | |
| C07K 16/26 | (2006.01) | |
| C07K 16/28 | (2006.01) | |
| C07K 16/38 | (2006.01) | |
| C07K 16/40 | (2006.01) | |

(52) U.S. Cl.
CPC ....... *G01N 33/57434* (2013.01); *C07K 16/18* (2013.01); *C07K 16/22* (2013.01); *C07K 16/24* (2013.01); *C07K 16/243* (2013.01); *C07K 16/244* (2013.01); *C07K 16/245* (2013.01); *C07K 16/246* (2013.01); *C07K 16/249* (2013.01); *C07K 16/26* (2013.01); *C07K 16/2821* (2013.01); *C07K 16/2833* (2013.01); *C07K 16/2839* (2013.01); *C07K 16/2878* (2013.01); *C07K 16/38* (2013.01); *C07K 16/40* (2013.01); *C07K 2317/622* (2013.01); *G01N 2570/00* (2013.01)

(58) Field of Classification Search
None
See application file for complete search history.

(56) References Cited

U.S. PATENT DOCUMENTS

2009/0017463 A1    1/2009   Bhowmick

FOREIGN PATENT DOCUMENTS

WO    2009/036427 A2    3/2009

OTHER PUBLICATIONS

Goldstein et al (Cancers, 2011, 3(4): 4281-4293).*
Tockman et al (Cancer Res., 1992, 52:2711s-2718s).*
Ueda et al (Anticancer Research, 2005, 25: 4595-4598).*
Sonpavde et al (Proceedings of the 101st Annual Meeting of the American Association for Cancer Research, 2010, Cancer Research, 70(8 Suppl): Abstract nr LB-80).*
Sen-Ong et al (Cancer Research, 2003, 63: 3296-3301).*
Lin, Daniel W. et al., "Genetic Variants in the LEPR, CRY1, RNASEL, IL4, and ARVCF Genes Are Prognostic Markers of Prostate Cancer-Specific Mortality", Cancer Epidemiol. Biomarkers Prev., 20(9): 1928-1936 (2011).
Mechergmi, Vosra Bouranni et al., "The Profile of Prostate Epithelial Cyto9kines and its Impact on Sera Prostate Specific Antigens Levels", Inflammation, 12(32(3): 202-210 (2009).
Nordstrom, Malin et al., "Identification of plasma protein profiles associated with risk groups of prostate cancer patients", Proteomics Clin. Appl., 8: 951-962 (2014).
Pepe, Margaret Sullivan et al., "Phases of Biomarker Development for Early Detection of Cancer", Journal of the National Cancer Institute, 93(14): 1054-1061 (2001).
Pepe, Margaret S. et al., "Pivotal Evaluation of the Accuracy of a Biomarker Used for Classification or Prediction: Standards for Study Design", JNCI, 100(20): 1432-1438 (2008).
Ricote, Monica et al., "Interleukin-1 (IL-1 and IL-1 ) and Its Receptors (IL-1RI , IL-1RII, and IL-1Ra) in Prostate Carcinoma", Cancer, 100(7): 1388-1396 (2004).
Xie, Hongbo et al., "Mining of Microarray, Proteomics and Clinical Data for Improved Identification of Chronic Fatigue Syndrome", Jan. 1, 2006, XP055303511.
Tazaki, Eri et al., "Serum cytokine profiles in patients with prostate carcinoma", Experimental and Therapeutic Medicine, 2: 887-891 (2011).
Wingren, C. et al., "Design of recombinant antibody microarrays for complex proteome analysis: choice of sample labeling-tag and solid support", P)roteomics, 7(17): 3055-65 (2007) [Abstract only].
Wise, G.J. et al.,. "Cytokine variations in patients with hormone treated prostate cancer", J. Urol., 164(3 Pt. 1): 722-725 (2000).

* cited by examiner

*Primary Examiner* — Sean E Aeder
(74) *Attorney, Agent, or Firm* — Kathleen D. Rigaut; Dann, Dorfman, Herrell and Skillman, P.C.

(57) ABSTRACT

The invention provides a method for determining prostate cancer-associated disease state in an individual comprising or consisting of the steps of: (a) providing a sample to be tested from the individual; and (b) determining a biomarker signature of the test sample by measuring the expression in the test sample of one or more biomarkers selected from the group defined in Table 1; wherein the expression in the test sample of the one or more biomarkers selected from the group defined in Table 1 is indicative of one or more prostate cancer-associated disease state in the individual. The invention also provides arrays and kits for use in the same.

25 Claims, 8 Drawing Sheets

SEQUENCE LISTING

<160> NUMBER OF SEQ ID NOS: 2

<210> SEQ ID NO 1
<211> LENGTH: 242
<212> TYPE: PRT
<213> ORGANISM: Homo sapiens

<400> SEQUENCE: 1

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Gly Phe His Trp Val Arg Gln Ala Pro Gly Lys Gly Leu Glu
        35                  40                  45

Trp Val Ser Leu Ile Ser Trp Asp Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                 85                  90                  95

Tyr Cys Ala Arg Gly Thr Trp Phe Asp Pro Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Gln Ser Val Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Asn Asn Ala Val Asn Trp Tyr Gln Gln Leu Pro Gly Thr Ala
                165                 170                 175

Pro Lys Leu Leu Ile Tyr Arg Asn Asn Gln Arg Pro Ser Gly Val Pro
                180                 185                 190

Asp Arg Phe Ser Gly Ser Lys Ser Gly Thr Ser Ala Ser Leu Ala Ile
            195                 200                 205

Ser Gly Leu Arg Ser Glu Asp Glu Ala Asp Tyr Tyr Cys Ala Ala Trp
        210                 215                 220

Asp Asp Ser Leu Ser Trp Val Phe Gly Gly Gly Thr Lys Leu Thr Val
225                 230                 235                 240

Leu Gly

<210> SEQ ID NO 2
<211> LENGTH: 31
<212> TYPE: PRT
<213> ORGANISM: Artificial Sequence
<220> FEATURE:
<223> OTHER INFORMATION: 6 x histidine affinity tag

<400> SEQUENCE: 2

Asp Tyr Lys Asp His Asp Gly Asp Tyr Lys Asp His Asp Ile Asp Tyr
1               5                   10                  15

Lys Asp Asp Asp Asp Lys Ala Ala Ala His His His His His His
                20                  25                  30
```

METHODS AND ARRAYS FOR USE IN THE SAME

Figure 1:
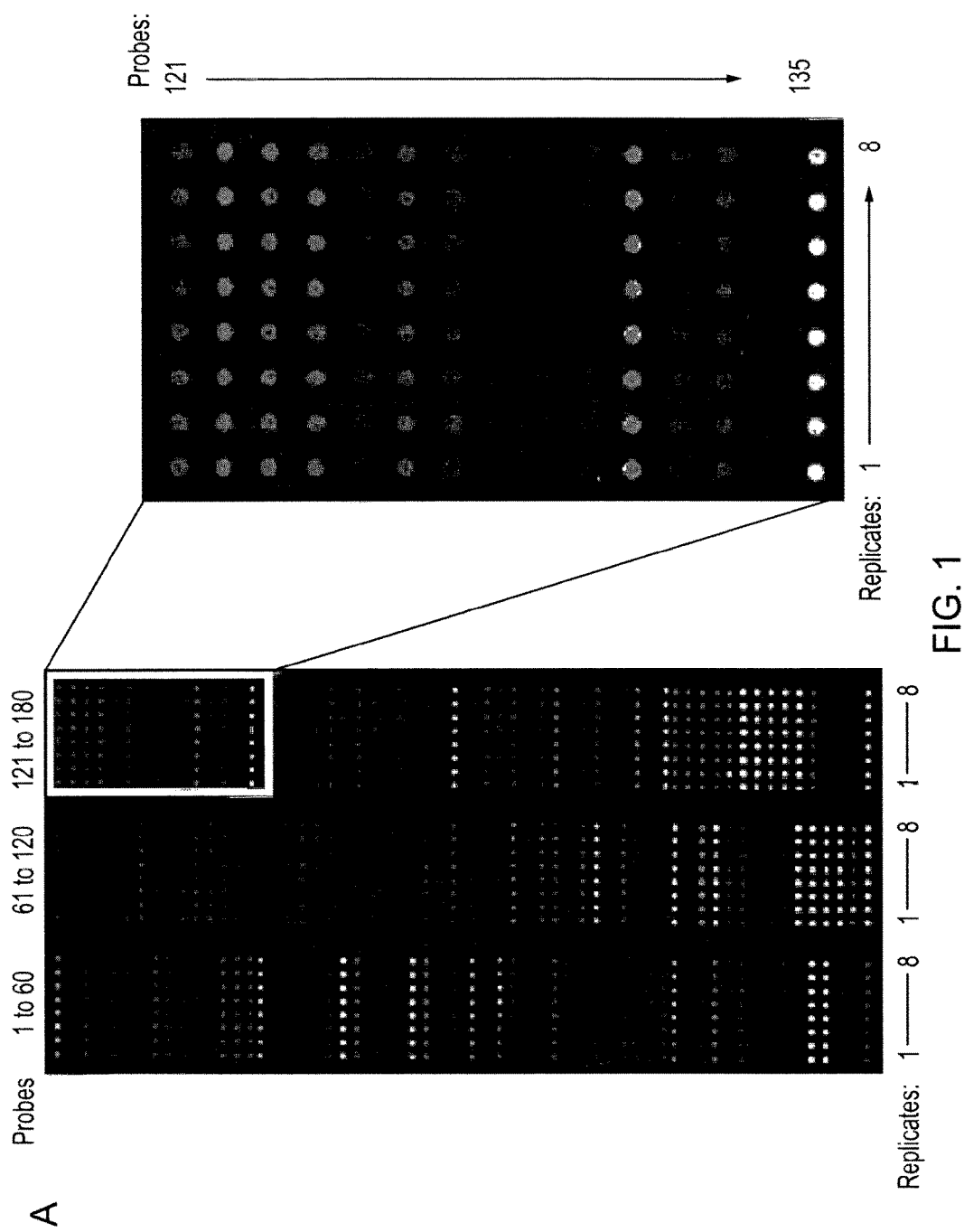
Figure 1:
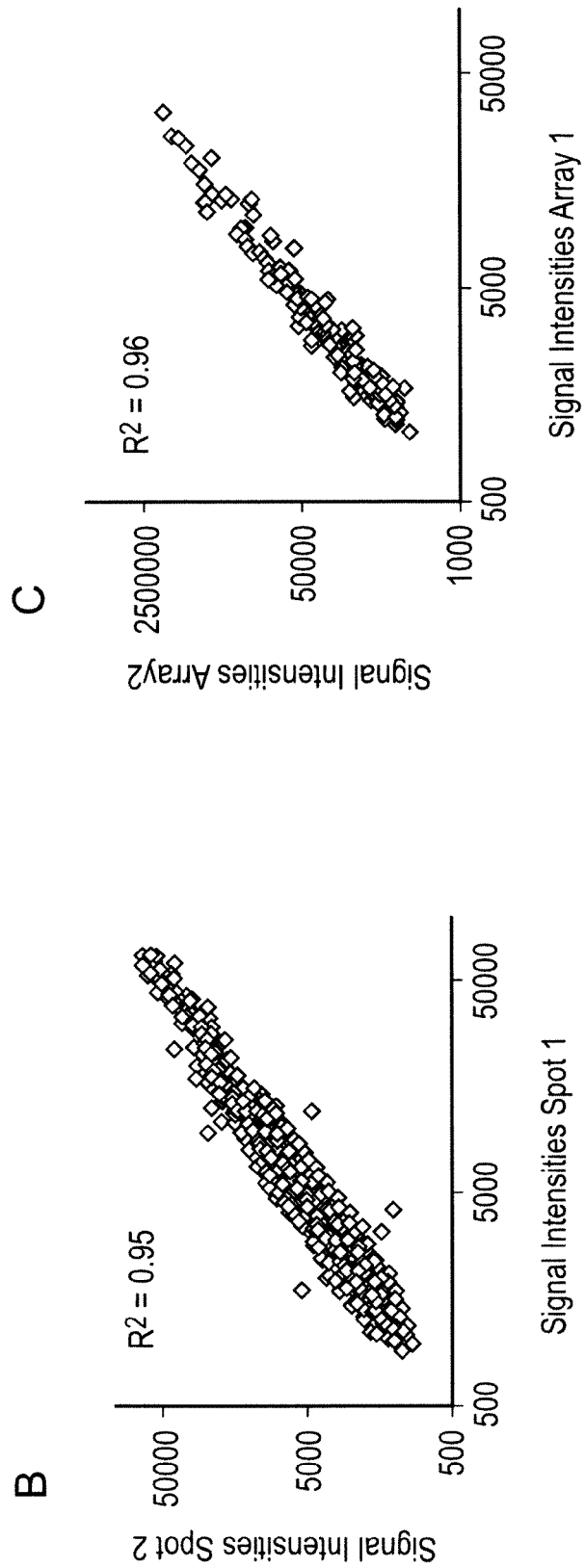

The present application is § 371 application of PCT/EP2014/056630 filed 2 Apr. 2014 which claims priority to GB Application No. 1305940.7 filed 2 Apr. 2013, the entire disclosure of each being incorporated by reference herein.

FIELD OF THE INVENTION

The present invention provides methods for determining a prostate cancer-associated disease state, as well as arrays and kits for use in such methods.

BACKGROUND OF THE INVENTION

Early detection of prostate cancer (PC) using prostate-specific antigen (PSA) in blood reduces PC-death among unscreened men. However, due to modest specificity of PSA at commonly used cut-offs, there are urgent needs for additional biomarkers contributing enhanced risk classification among men with modestly elevated PSA.

Prostate cancer (PC) is the second leading cause of cancer related deaths in western countries [1] and in order to improve the prognosis of PC patients, early and specific diagnosis is crucial. The blood-based biomarker prostate specific antigen (PSA) was introduced in the clinics in the late 1980's and is today used as an indicator of risk for PC and as one parameter for further testing of patient biopsies [2, 3]. The introduction of PSA has resulted in an increased number of early diagnosed PC cases, but the moderate specificity of PSA for malignant disease has raised key concerns regarding the cost and potential side-effects of unnecessary biopsies as well as the risk of over-diagnosis and over-treatment [2-4]. In fact, 65-75% of the men selected for biopsy based on total serum PSA levels (tPSA) (≤4 ng/ml), do not have PC (www.cancer.org). Hence, in order to improve the risk classification enabling clinicians to select adequate patients for biopsy testing, additional and/or more specific biomarkers needs to be defined.

In order to improve the specificity when testing for PC, several attempts have been made to combine the tPSA value with other parameters, such as PSA change over time (PSA velocity), PSA in relation to prostate volume (PSA density), or age specific ranges of PSA [2, 3]. However, no or only modest improvements of the diagnostic power of the tPSA assay have so far been observed [2]. In contrast, differentiating between tPSA and free (unbound) PSA has proven to enhance the assay performance, especially for men with mid-range (4-10 ng/ml) levels of tPSA. In fact, men having a ratio of free PSA to tPSA (% fPSA) below 18-25% have shown to be associated with a significantly higher risk of having PC [5-7]. Still, 25-50% of this particular patient group does not have PC, but they are all selected for biopsy testing [7, 8]. Recently, a panel of four kallikrein markers has been indicated as potential predictors of biopsy outcome [9, 10], and that the combination of tPSA, free PSA, with the free PSA sub-fraction called 2proPSA might also improve diagnostic accuracy [11].

However, there remains a significant unmet clinical need for additional, more specific biomarkers that could be used to detect prostate cancer and/or stratify prostate cancer according to risk, particularly prior to biopsy testing and/or therapy.

DISCLOSURE OF THE INVENTION

Major efforts have also been pursued in order to define additional, novel serum biomarkers associated with PC, initially using various classical biochemical technologies. To date, human kallikrein 2 [12, 13], urokinase-type plasminogen activator [14], [11] transforming growth factor β1 (TGF-β1) [3, 15, 16], and interleukin-6 (IL-6) [16-18] have in particular been indicated as potential serum markers. Albeit promising, further validation studies will be required to explore and confirm the prognostic capabilities of these markers [2-4]. Moreover, additional potential PC markers have also been indicated using traditional proteomic techniques [19, 20], but these observations remain to be validated using independent patient cohorts [21]. In addition, serious technical issues have also been raised regarding the assay sensitivity, dynamic range, and/or throughput [22, 23]. To this end, affinity proteomics have been established as a high-throughput alternative capable of targeting non-fractionated proteomes, e.g., plasma and serum, in a multiple, sensitive, and rapid manner [24-27].

In this context, the present inventors have previously designed a recombinant single chain fragment variable (scFv) antibody microarray platform for protein expression profiling of complex proteomes [26, 28, 29]. Using this affinity proteomic technology platform, the present inventors have been able to profile a wide range of crude, directly labeled proteomes, including serum, plasma, urine, intact cells, cell lysates, and tissue extracts [28, 30, 31] in a rapid, sensitive and reproducible manner. We have demonstrated that the platform could be used to identify candidate biomarker signatures for e.g., diagnosis, prognosis, classification, and for evidence-based therapy selection [32-37].

The present inventors investigated whether affinity proteomics could be used to validate and even further refine risk group classification targeting plasma samples from routine PSA measurements with the patient samples being stratified into four biochemically defined risk groups according to current established clinical practice [38-41]. The data showed that plasma protein signatures could be identified that were able to pin-point PC ("a malignant biomarker signature") and to stratify patients into current as well as new subgroups related to PC risk, which in the long-term has the potential to contribute to more individualized treatment of PC.

Accordingly, a first aspect of the invention provides a method for determining a prostate cancer-associated disease state in an individual comprising or consisting of the steps of:
 a) providing a sample to be tested from the individual;
 b) determining a biomarker signature of the test sample by measuring the expression in the test sample of one or more biomarkers selected from the group defined in Table 1;
wherein the expression in the test sample of the one or more biomarkers selected from the group defined in Table 1 is indicative of one or more prostate cancer-associated disease state in the individual.

By "prostate cancer-associated disease state" we mean the presence or absence of prostate cancer, the prostate cancer group or subgroup (A, B C, C1, C2 or D, defined below) and/or the likelihood of prostate cancer occurring in an individual (preferably, within a given timeframe).

By "biomarker" we mean a naturally-occurring biological molecule, or component or fragment thereof, the measurement of which can provide information useful in determining a prostate cancer-associated disease state, e.g., prognosis of prostate cancer. For example, the biomarker may be a naturally-occurring protein or carbohydrate moiety, or an antigenic component or fragment thereof.

Preferably the sample to be tested is provided from a mammal. The mammal may be any domestic or farm animal. Preferably, the mammal is a rat, mouse, guinea pig, cat, dog, horse or a primate. Most preferably, the mammal is human. Preferably the sample is a cell or tissue sample (or derivative thereof) comprising or consisting of crude blood, pre-fractionated blood, plasma, plasma cells, prostate cells or equally preferred, protein or nucleic acid derived from a cell or tissue sample comprising or consisting of plasma, plasma cells or prostate cells. Preferably test and control samples are derived from the same species.

In one embodiment the method according to the first aspect of the invention further comprises or consists of the steps of:
  c) providing one or more control sample from an individual not afflicted with prostate cancer;
  d) determining a biomarker signature of the control sample by measuring the expression in the control sample of the one or more biomarkers measured in step (b);
wherein the one or more prostate cancer-associated disease state is identified in the event that the expression in the test sample of the one or more biomarkers measured in step (b) is different from the expression in the control sample of the one or more biomarkers measured in step (d).

In a further or additional embodiment the method comprises or consists of the steps of:
  e) providing a control sample from an individual afflicted with prostate cancer;
  f) determining a biomarker signature of the control sample by measuring the expression in the control sample of the one or more biomarkers measured in step (b);
wherein the one or more prostate cancer-associated disease state is identified in the event that the expression in the test sample of the one or more biomarkers measured in step (b) corresponds to the expression in the control sample of the one or more biomarkers measured in step (f).

By "corresponds to the presence and/or amount in a control sample" we mean the presence and or amount is identical to that of a control sample provided in step (e); or closer to that of a control sample provided in step (e) (e.g., a positive control sample) than to a control sample provided in step (c) (e.g., a negative control sample) (or to predefined reference values representing the same). Preferably the presence and/or amount is at least 60% of that of a control sample provided in step (e), for example, at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

By "is different to the presence and/or amount in a control sample" we mean the presence and or amount differs from that of the control sample provided in step (c) (or to predefined reference values representing the same). Preferably the presence and/or amount is no more than 40% of that of the control sample comprising or consisting prostate cancer cells, for example, no more than 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or 0%.

Preferably, the one or more control samples are age-and/or sex-matched for the individual to be tested. In other words, the healthy individual is approximately the same age (e.g. within 5 years) and is the same sex as the individual to be tested.

Preferably, the presence and/or amount in the test sample of the one or more biomarkers measured in step (b) are compared against predetermined reference values.

Hence, it is preferred that the presence and/or amount in the test sample of the one or more biomarker measured in step (b) is significantly different (i.e. statistically different) from the presence and/or amount of the one or more biomarker measured in step (d) or the predetermined reference values. Hence, it is preferred that the presence and/or amount in the test sample of the one or more biomarker measured in step (b) significantly corresponds to (i.e. statistically similar to) the presence and/or amount of the one or more biomarker measured in step (f) or the predetermined reference values. For example, as discussed in the accompanying Examples, significant difference between the presence and/or amount of a particular biomarker in the test and control samples may be classified as those where $p<0.05$ (for example, where $p<0.04$, $p<0.03$, $p<0.02$ or where $p<0.01$).

Preferably step (b) comprises or consists of measuring the presence and/or amount in the test sample of one or more biomarkers selected from the group defined in Table 1, for example at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, or 67 biomarkers selected from the group defined in Table 1.

Step (b) may comprise or consist of measuring the expression of IL-4. Alternatively or additionally, step (b) may comprise or consist of measuring the expression of IL-12. Alternatively or additionally, step (b) may comprise or consist of measuring the expression of IL-9. Alternatively or additionally, step (b) may comprise or consist of measuring the expression of IL-1a. Alternatively or additionally, step (b) may comprise or consist of measuring the expression of HLA-DR. Alternatively or additionally, step (b) may comprise or consist of measuring the expression of IL-3. Alternatively or additionally, step (b) may comprise or consist of measuring the expression of ICAM. Alternatively or additionally, step (b) may comprise or consist of measuring the expression of CD40. Alternatively or additionally, step (b) may comprise or consist of measuring the expression of IL-18. Alternatively or additionally, step (b) may comprise or consist of measuring the expression of IL-1b. Alternatively or additionally, step (b) may comprise or consist of measuring the expression of GLP-1. Alternatively or additionally, step (b) may comprise or consist of measuring the expression of IL-11. Alternatively or additionally, step (b) may comprise or consist of measuring the expression of VEGF. Alternatively or additionally, step (b) may comprise or consist of measuring the expression of Cystatin C. Alternatively or additionally, step (b) may comprise or consist of measuring the expression of C1-INH. Alternatively or additionally, step (b) may comprise or consist of measuring the expression of MCP-3. Alternatively or additionally, step (b) may comprise or consist of measuring the expression of IL-13. Alternatively or additionally, step (b) may comprise or consist of measuring the expression of TNF-β. Alternatively or additionally, step (b) may comprise or consist of measuring the expression of C1s. Alternatively or additionally, step (b) may comprise or consist of measuring the expression of Integrin α-10. Alternatively or additionally, step (b) may comprise or consist of measuring the expression of C3. Alternatively or additionally, step (b) may comprise or consist of measuring the expression of GLP-1R. Alternatively or additionally, step (b) may comprise or consist of measuring the expression of IgM. Alternatively or additionally, step (b) may comprise or consist of measuring the expression of IL-16. Alternatively or additionally, step (b) may comprise or consist of measuring the expression of TM peptide. Alternatively or additionally, step (b) may comprise or consist of measuring the expression of Mucine-1. Alternatively or additionally, step (b) may comprise or consist of measuring the expression of IL-2. Alternatively or additionally, step (b) may comprise or consist of measuring the expression of IFN-γ. Alternatively or additionally, step (b) may comprise or consist of measuring the expression of CD40 ligand. Alternatively or additionally, step (b) may comprise or consist of measuring the expression of IL-10. Alternatively or additionally, step (b) may comprise or consist of measuring the expression of GM-CSF. Alternatively or additionally, step (b) may comprise or consist of measuring the expression of Factor B. Alternatively or additionally, step (b) may comprise or consist of measuring the expression of C4. Alternatively or additionally, step (b) may comprise or consist of measuring the expression of Integrin α-11. Alternatively or additionally, step (b) may comprise or consist of measuring the expression of IL-8. Alternatively or additionally, step (b) may comprise or consist of measuring the expression of MCP-4. Alternatively or additionally, step (b) may comprise or consist of measuring the expression of LDL (1). Alternatively or additionally, step (b) may comprise or consist of measuring the expression of TNF-β (1). Alternatively or additionally, step (b) may comprise or consist of measuring the expression of IL-7. Alternatively or additionally, step (b) may comprise or consist of measuring the expression of Eotaxin. Alternatively or additionally, step (b) may comprise or consist of measuring the expression of Rantes. Alternatively or additionally, step (b) may comprise or consist of measuring the expression of β-galactosidase. Alternatively or additionally, step (b) may comprise or consist of measuring the expression of Leptin. Alternatively or additionally, step (b) may comprise or consist of measuring the expression of Mucin 1. Alternatively or additionally, step (b) may comprise or consist of measuring the expression of LDL (2). Alternatively or additionally, step (b) may comprise or consist of measuring the expression of JAK3. Alternatively or additionally, step (b) may comprise or consist of measuring the expression of IL-1β. Alternatively or additionally, step (b) may comprise or consist of measuring the expression of Properdin. Alternatively or additionally, step (b) may comprise or consist of measuring the expression of IL-5. Alternatively or additionally, step (b) may comprise or consist of measuring the expression of Apo-A1. Alternatively or additionally, step (b) may comprise or consist of measuring the expression of LDL. Alternatively or additionally, step (b) may comprise or consist of measuring the expression of TNF-α. Alternatively or additionally, step (b) may comprise or consist of measuring the expression of BTK. Alternatively or additionally, step (b) may comprise or consist of measuring the expression of TNF-β (2). Alternatively or additionally, step (b) may comprise or consist of measuring the expression of MCP-4 (1). Alternatively or additionally, step (b) may comprise or consist of measuring the expression of MCP-4 (2). Alternatively or additionally, step (b) may comprise or consist of measuring the expression of GLP. Alternatively or additionally, step (b) may comprise or consist of measuring the expression of Angiomotin. Alternatively or additionally, step (b) may comprise or consist of measuring the expression of MCP-1. Alternatively or additionally, step (b) may comprise or consist of measuring the expression of IL-6. Alternatively or additionally, step (b) may comprise or consist of measuring the expression of Lewis X. Alternatively or additionally, step (b) may comprise or consist of measuring the expression of C1q. Alternatively or additionally, step (b) may comprise or consist of measuring the expression of Sialyl Lewis X. Alternatively or additionally, step (b) may comprise or consist of measuring the expression of TGF-β. Alternatively or additionally, step (b) may comprise or consist of measuring the expression of IL-1ra. Alternatively or additionally, step (b) may comprise or consist of measuring the expression of TGF-β1. Alternatively or additionally, step (b) may comprise or consist of measuring the expression of PSA.

Hence, step (b) may not comprise measuring the expression of IL-4. Alternatively or additionally, step (b) may not comprise measuring the expression of IL-12. Alternatively or additionally, step (b) may not comprise measuring the expression of IL-9. Alternatively or additionally, step (b) may not comprise measuring the expression of IL-1a. Alternatively or additionally, step (b) may not comprise measuring the expression of HLA-DR. Alternatively or additionally, step (b) may not comprise measuring the expression of IL-3. Alternatively or additionally, step (b) may not comprise measuring the expression of ICAM. Alternatively or additionally, step (b) may not comprise measuring the expression of CD40. Alternatively or additionally, step (b) may not comprise measuring the expression of IL-18. Alternatively or additionally, step (b) may not comprise measuring the expression of IL-1b. Alternatively or additionally, step (b) may not comprise measuring the expression of GLP-1. Alternatively or additionally, step (b) may not comprise measuring the expression of IL-11. Alternatively or additionally, step (b) may not comprise measuring the expression of VEGF. Alternatively or additionally, step (b) may not comprise measuring the expression of Cystatin C. Alternatively or additionally, step (b) may not comprise measuring the expression of C1-INH. Alternatively or additionally, step (b) may not comprise measuring the expression of MCP-3. Alternatively or additionally, step (b) may not comprise measuring the expression of IL-13. Alternatively or additionally, step (b) may not comprise measuring the expression of TNF-β. Alternatively or additionally, step (b) may not comprise measuring the expression of C1s. Alternatively or additionally, step (b) may not comprise measuring the expression of Integrin α-10. Alternatively or additionally, step (b) may not comprise measuring the expression of C3. Alternatively or additionally, step (b) may not comprise measuring the expression of GLP-1R. Alternatively or additionally, step (b) may not comprise measuring the expression of IgM. Alternatively or additionally, step (b) may not comprise measuring the expression of IL-16. Alternatively or additionally, step (b) may not comprise measuring the expression of TM peptide. Alternatively or additionally, step (b) may not comprise measuring the expression of Mucine-1. Alternatively or additionally, step (b) may not comprise measuring the expression of IL-2. Alternatively or additionally, step (b) may not comprise measuring the expression of IFN-γ. Alternatively or additionally, step (b) may not comprise measuring the expression of CD40 ligand. Alternatively or additionally, step (b) may not comprise measuring the expression of IL-10. Alternatively or additionally, step (b) may not comprise measuring the expression of GM-CSF. Alternatively or additionally, step (b) may not comprise measuring the expression of Factor B. Alternatively or additionally, step (b) may not comprise measuring the expression of C4. Alternatively or additionally, step (b) may not comprise measuring the expression of Integrin α-11. Alternatively or additionally, step (b) may not comprise measuring the expression of IL-8. Alternatively or additionally, step (b) may not comprise measuring the expression of MCP-4. Alternatively or additionally, step (b) may not comprise measuring the expression of LDL (1). Alternatively or additionally, step (b) may not comprise measuring the expression of TNF-β (1). Alternatively or additionally, step (b) may not comprise measuring the expression of IL-7. Alternatively or additionally, step (b) may not comprise measuring the expression of Eotaxin. Alternatively or additionally, step (b) may not comprise measuring the expression of Rantes. Alternatively or additionally, step (b) may not comprise measuring the expression of β-galactosidase. Alternatively or additionally, step (b) may not comprise measuring the expression of Leptin. Alternatively or additionally, step (b) may not comprise measuring the expression of Mucin 1. Alternatively or additionally, step (b) may not comprise measuring the expression of LDL (2). Alternatively or additionally, step (b) may not comprise measuring the expression of JAK3. Alternatively or additionally, step (b) may not comprise measuring the expression of IL-1β. Alternatively or additionally, step (b) may not comprise measuring the expression of Properdin. Alternatively or additionally, step (b) may not comprise measuring the expression of IL-5. Alternatively or additionally, step (b) may not comprise measuring the expression of Apo-A1. Alternatively or additionally, step (b) may not comprise measuring the expression of LDL. Alternatively or additionally, step (b) may not comprise measuring the expression of TNF-α. Alternatively or additionally, step (b) may not comprise measuring the expression of BTK. Alternatively or additionally, step (b) may not comprise measuring the expression of TNF-β (2). Alternatively or additionally, step (b) may not comprise measuring the expression of MCP-4 (1). Alternatively or additionally, step (b) may not comprise measuring the expression of MCP-4 (2). Alternatively or additionally, step (b) may not comprise measuring the expression of GLP. Alternatively or additionally, step (b) may not comprise measuring the expression of Angiomotin. Alternatively or additionally, step (b) may not comprise measuring the expression of MCP-1. Alternatively or additionally, step (b) may not comprise measuring the expression of IL-6. Alternatively or additionally, step (b) may not comprise measuring the expression of Lewis X. Alternatively or additionally, step (b) may not comprise measuring the expression of C1q. Alternatively or additionally, step (b) may not comprise measuring the expression of Sialyl Lewis X. Alternatively or additionally, step (b) may not comprise measuring the expression of TGF-β. Alternatively or additionally, step (b) may not comprise measuring the expression of IL-1ra. Alternatively or additionally, step (b) may not comprise measuring the expression of TGF-β1. Alternatively or additionally, step (b) may not comprise measuring the expression of PSA.

By "expression" we mean the level or amount of a gene product such as mRNA or protein.

By "TM peptide" we mean a peptide derived from a 10TM protein, to which the scFv antibody construct of SEQ ID NO:1 below has specificity (wherein the CDR sequences are underlined):

[SEQ ID NO: 1]
MAEVQLLESGGGLVQPGGSLRLSCAASGFT*FSSYGFHWVRQAPG*KGLEWV

*SLISWDGGSTYYADSVKGR*FTISRDNSKNTLYLQMNSLRAEDTAVYYCAR

GTWFDPWGQGTLVTVSSGGGGSGGGGSGGGGSQSVLTQPPSASGTPGQRV

-continued
TISCS*GSSSNIGNNAVN*WYQQLPGTAPKLLIY*RNNQRPS*GVPDRFSGSKS

GTSASLAISGLRSEDEADYYC*AAWDDSLSWV*FGGGTKLTVLG

Hence, this scFv may be used or any antibody, or antigen binding fragment thereof, that competes with this scFv for binding to the 10TM protein. For example, the antibody, or antigen binding fragment thereof, may comprise the same CDRs as present in SEQ ID NO:1.

It will be appreciated by persons skilled in the art that such an antibody may be produced with an affinity tag (e.g. at the C-terminus) for purification purposes. For example, an affinity tag of SEQ ID NO:2 below may be utilised:

[SEQ ID NO: 2]
DYKDHDGDYKDHDIDYKDDDDKAAAHHHHHH

Methods of detecting and/or measuring the concentration of protein and/or nucleic acid are well known to those skilled in the art, see for example Sambrook and Russell, 2001, Cold Spring Harbor Laboratory Press.

Preferred methods for detection and/or measurement of protein include Western blot, North-Western blot, immunosorbent assays (ELISA), antibody microarray, tissue microarray (TMA), immunoprecipitation, in situ hybridisation and other immunohistochemistry techniques, radioimmunoassay (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference. Antibody staining of cells on slides may be used in methods well known in cytology laboratory diagnostic tests, as well known to those skilled in the art.

Typically, ELISA involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemi-luminescent systems based on enzymes such as luciferase can also be used.

Conjugation with the vitamin biotin is frequently used since this can readily be detected by its reaction with enzyme-linked avidin or streptavidin to which it binds with great specificity and affinity.

Hence, in one embodiment step (b) comprises or consists of measuring the expression of one or more of the biomarkers listed in Table 1 (A), for example, at least 2, 3 or 4 of the biomarkers listed in Table 1 (A). The method may comprise or consist of measuring in step (b) the expression of each the biomarkers listed in Table 1(A).

In one embodiment step (b) may comprise or consist of measuring the expression of one or more of the biomarkers listed in Table 1(B), for example at least 2, 3, 4, 5 or 6 of the biomarkers listed in Table 1 (B). The method may comprise or consist of measuring in step (b) the expression of each the biomarkers listed in Table 1(B).

In an alternative or additional embodiment the method comprises or consists of measuring, in step (b), the expression of one or more biomarkers from the biomarkers listed in Table 1(C), for example at least 2, 3, 4, 5, 6, 7 or 8 of the biomarkers listed in Table 1(C). The method may comprise or consist of measuring in step (b) the expression of each the biomarkers listed in Table 1(C).

In an alternative or additional embodiment the method comprises or consists of measuring, in step (b), the expression of one or more biomarkers from the biomarkers listed in Table 1(D), for example at least 2, 3, 4, 5, 6, 7, 8, 9, 10 or 11 of the biomarkers listed in Table 1(D). The method may comprise or consist of measuring in step (b) the expression of each the biomarkers listed in Table 1(D).

In an alternative or additional embodiment the method comprises or consists of measuring, in step (b), the expression of one or more biomarkers from the biomarkers listed in Table 1(E), for example at least 2, 3, 4, 5, 6, 7 or 8 of the biomarkers listed in Table 1(E). The method may comprise or consist of measuring in step (b) the expression of each the biomarkers listed in Table 1(E).

In an alternative or additional embodiment the method comprises or consists of measuring, in step (b), the expression of one or more biomarkers from the biomarkers listed in Table 1(F), for example at least 2, 3, 4, 5, 6, 7 or 8 of the biomarkers listed in Table 1(F). The method may comprise or consist of measuring in step (b) the expression of each the biomarkers listed in Table 1(F).

In an alternative or additional embodiment the method comprises or consists of measuring, in step (b), the expression of one or more biomarkers from the biomarkers listed in Table 1(G), for example at least 2, 3, 4, 5, 6, 7 or 8 of the biomarkers listed in Table 1(G). The method may comprise or consist of measuring in step (b) the expression of each the biomarkers listed in Table 1(G).

In an alternative or additional embodiment the method comprises or consists of measuring, in step (b), the expression of one or more biomarkers from the biomarkers listed in Table 1(H), for example at least 2, 3, 4 or 5 of the biomarkers listed in Table 1(H). The method may comprise or consist of measuring in step (b) the expression of each the biomarkers listed in Table 1(H).

In an alternative or additional embodiment the method comprises or consists of measuring, in step (b), the expression of one or more biomarkers from the biomarkers listed in Table 1(I), for example at least 2, 3, 4, 5, 6, 7, 8 or 9 of the biomarkers listed in Table 1(I). The method may comprise or consist of measuring in step (b) the expression of each the biomarkers listed in Table 1(I).

In an alternative or additional embodiment step (b) comprises or consists of measuring the expression of one or more biomarkers from the biomarkers listed in Table 2(A), for example at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the biomarkers listed in Table 2(A). Step (b) may comprise or consist of measuring the expression of all of the biomarkers listed in Table 2(A).

In an alternative or additional embodiment step (b) comprises or consists of measuring the expression of one or more biomarkers from the biomarkers listed in Table 2(B), for example at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 of the biomarkers listed in Table 2(B). Step (b) may comprise or consist of measuring the expression of all of the biomarkers listed in Table 2(B).

In an alternative or additional embodiment step (b) comprises or consists of measuring the expression of one or more biomarkers from the biomarkers listed in Table 2 (C), for example at least 2, 3, 4, 5, 6, 7, 8, 9, 10, 11, 12, 13, 14, 15, 16, 17, 18, 19, 20, 21, 22, 23, 24, 25, 26, 27, 28 or 29 of the biomarkers listed in Table 2(C). Step (b) may comprise or consist of measuring the expression of all of the biomarkers listed in Table 2 (C).

In an alternative or additional embodiment step (b) comprises or consists of measuring the expression of one or more biomarkers from the biomarkers listed in Table 2 (D), for example at least 2 or 3 of the biomarkers listed in Table 2(D). Step (b) may comprise or consist of measuring the expression of all of the biomarkers listed in Table 2 (D).

In an alternative or additional embodiment step (b) comprises or consists of measuring the expression of one or more biomarkers from the biomarkers listed in Table 2 (E), for example at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 of the biomarkers listed in Table 2(E). Step (b) may comprise or consist of measuring the expression of all of the biomarkers listed in Table 2 (E).

In an alternative or additional embodiment step (b) comprises or consists of measuring the expression of one or more biomarkers from the biomarkers listed in Table 2 (F), for example at least 2, 3, 4, 5, 6, 7, 8, 9, 10, 11, 12, 13, 14, 15 or 16 of the biomarkers listed in Table 2(F). Step (b) may comprise or consist of measuring the expression of all of the biomarkers listed in Table 2 (F).

In an alternative or additional embodiment step (b) comprises or consists of measuring the expression of one or more biomarkers from the biomarkers listed in Table 2 (G), for example at least 2, 3, 4, 5, 6, 7, 8, 9, 10, 11, 12, 13 or 14 of the biomarkers listed in Table 2(G). Step (b) may comprise or consist of measuring the expression of all of the biomarkers listed in Table 2 (G).

In an alternative or additional embodiment step (b) comprises or consists of measuring the expression of one or more biomarkers from the biomarkers listed in Table 2 (H), for example at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46 of the biomarkers listed in Table 2(H). Step (b) may comprise or consist of measuring the expression of all of the biomarkers listed in Table 2 (H).

In an alternative or additional embodiment step (b) comprises or consists of measuring the expression of one or more biomarkers from the biomarkers listed in Table 2 (I), for example at least 2, 3, 4, 5, 6, 7, 8, 9, 10, 11, 12, 13, 14, 15, 16, 17, 18, 19, 20, 21, 22 or 23 of the biomarkers listed in Table 2(I). Step (b) may comprise or consist of measuring the expression of all of the biomarkers listed in Table 2 (I).

In an alternative or additional embodiment step (b) comprises or consists of measuring the expression of one or more biomarkers from the biomarkers listed in Table 2 (J), for example at least 2, 3, 4, 5, 6, 7, 8, 9, 10, 11, 12, 13, 14, 15, 16, 17, 18, 19, 20, 21, 22, 23, 24, 25, 26, 27, 28 or 29 of the biomarkers listed in Table 2(J). Step (b) may comprise or consist of measuring the expression of all of the biomarkers listed in Table 2 (J).

In an alternative or additional embodiment step (b) comprises or consists of measuring the expression of one or more biomarkers from the biomarkers listed in Table 2 (K), for example at least 2, 3, 4, 5, 6, 7, 8, 9, 10, 11, 12 or 13 of the biomarkers listed in Table 2(K). Step (b) may comprise or consist of measuring the expression of all of the biomarkers listed in Table 2 (K).

In an alternative or additional embodiment, the one or more prostate cancer-associated disease state is or includes determining the likelihood of the occurrence of clinically significant prostate cancer. Preferably, the likelihood of the occurrence of clinically significant prostate cancer within a particular time-frame is determined, for example, within, 1 month, 2 months, 3 months, 5 months, 6 months, 1 year, 2 years, 3 years, 4 years, 5 years, 6 years, 7 years, 8 years, 9 years, 10 years, 15 years, 20 years, 25 years, 30 years, 25 years, 40 years, 55 years, 60 years, 75 years, 80 years or within the natural lifespan of the individual being tested.

In an alternative or additional embodiment, the method is for differentiating between risk group A (low risk), risk group B (moderate risk), risk group C (increased risk), risk subgroup C1 (moderately increased risk), risk subgroup C2 (importantly increased risk) and risk group D (high risk).

In one embodiment, by "low risk" we mean a 2% or lower chance of having or developing clinically significant prostate cancer within a particular time-frame, for example, ≤1.5%, ≤1.0%, ≤0.5%, ≤0.1%, ≤0.05%, ≤0.01%, ≤0.005% or ≤0.001% (or between any two of those points). In one embodiment, by "moderate risk" we mean >2% and ≤10% chance of having or developing clinically significant prostate cancer within a particular time-frame, for example, ≤9%, ≤8%, ≤7%, ≤6%, ≤5%, ≤4%, ≤3% or ≤2.5% (or between any two of those points). In one embodiment, by "increased risk" we mean >10% and ≤50% chance of having or developing clinically significant prostate cancer within a particular time-frame, for example, ≤45%, ≤40%, ≤35%, ≤30%, ≤25%, ≤20%, ≤15%, ≤12.5%, ≤11.0% or ≤10.5% (or between any two of those points). In one embodiment, by "importantly increased risk" we mean >50% and ≤85% chance of having or developing clinically significant prostate cancer within a particular time-frame, for example, ≤80%, ≤75%, ≤70%, ≤65%, ≤60%, ≤55%, ≤52.5%, ≤51.0% or ≤50.5% (or between any two of those points). In one embodiment, by "high" we mean >90% and ≤100% chance of having or developing clinically significant prostate cancer within a particular time-frame, for example, 100%, ≤100%, ≤99%, ≤98%, ≤97%, ≤96%, ≤95%, ≤92.5%, ≤90%, ≤87.5%, ≤86%, ≤85.5% or ≤85.1% (or between any two of those points). Preferably, the 'low', 'moderate', 'increased', 'importantly increased' and 'high' risk groups are contiguous; hence, where using an intermediate value for one risk group, the adjacent risk groups are adjusted accordingly. For example, if a low risk value of ≤1.0% was used, the moderate risk group would span from >1.0%. Preferably, particular time-frame is 1 month, 2 months, 3 months, 5 months, 6 months, 1 year, 2 years, 3 years, 4 years, 5 years, 6 years, 7 years, 8 years, 9 years, 10 years, 15 years, 20 years, 25 years, 30 years, 25 years, 40 years, 55 years, 60 years, 75 years, 80 years or within the natural lifespan of the individual being tested. Most preferably, 5 years.

These groups can be defined based on the levels of % free and total PSA: group A having tPSA ≤0.70 ng/ml; group B having tPSA of 2.1-8.0 ng/ml with % fPSA ≤27.9%; group C having tPSA of 5.0-10-3 ng/ml with % fPSA ≤12.6% and group D having tPSA of 24.6-724 ng/ml. Group A and B patients require no treatment. Group C is diverse group and can be split into subgroups C1 and C2. Group C1 is more similar to groups A and B, i.e., with low risk for prostate cancer and thus there is low/no need for biopsy and treatment, while group C2 is more similar to group D, i.e., the cancer group and, thus, indicates the need for biopsy and treatment.

In one embodiment the method is for or includes differentiating between risk group A (low risk) and risk group D (high risk). In an alternative or additional embodiment the method is for or includes differentiating between risk group B (moderate risk) and risk group D (high risk). In an alternative or additional embodiment the method is for or includes differentiating between risk group C (increased risk) and risk group D (high risk). In an alternative or additional embodiment the method is for or includes differentiating between risk group A (low risk) and risk group B (moderate risk). In an alternative or additional embodiment the method is for or includes differentiating between risk subgroup C1 (moderately increased risk) and risk subgroup C2 (importantly increased risk). In an alternative or additional embodiment the method is for or differentiating between risk subgroup C1 (moderately increased risk) and risk group A (low risk). In an alternative or additional embodiment the method is for or includes differentiating between risk subgroup C1 (moderately increased risk) and risk group B (moderate risk). In an alternative or additional embodiment the method is for or includes differentiating between risk subgroup C1 (moderately increased risk) and risk group D (high risk). In an alternative or additional embodiment the method is for or includes differentiating between risk subgroup C2 (importantly increased risk) and risk group A (low risk). In an alternative or additional embodiment the method is for or includes differentiating between risk subgroup C2 (importantly increased risk) and risk group B (moderate risk). In an alternative or additional embodiment the method is for or includes differentiating between risk subgroup C2 (importantly increased risk) and risk group D (high risk).

However, in an alternative or additional embodiment the one or more prostate cancer-associated disease state is or includes determining the presence or absence of prostate cancer (i.e., the diagnosis of prostate cancer). Preferably, the diagnosis of prostate cancer comprises or consists of measuring, in step (b), the expression of one or more of the biomarkers listed in Table 1 (A), for example, at least 2, 3 or 4 of the biomarkers listed in Table 1 (A). The method may comprise or consist of measuring in step (b) the expression of each the biomarkers listed in Table 1(A). In one embodiment, the presence of prostate cancer is indicated by classification in risk subgroup C2 or D. In one embodiment, the presence of prostate cancer is indicated by classification in risk subgroup C2. In one embodiment, the presence of prostate cancer is indicated by classification in risk subgroup D. In one embodiment, where the presence of prostate cancer is indicated, the method comprises biopsy and/or treatment of the patient for prostate cancer according to current recommendations (e.g., surgical removal of cancer cells, radiotherapy and/or chemotherapy).

In one embodiment of the first aspect of the invention, step (b) comprises or consists of measuring the expression in the test sample of all of the biomarkers defined in Table 1 and/or Table 2.

In a further or additional embodiment, the individual not afflicted with prostate cancer (of step (c)) is not afflicted with any other prostate-related disorder. Preferably, the individual not afflicted with prostate cancer is not afflicted with any disease or condition. Most preferably, the individual not afflicted with prostate cancer is a healthy individual.

In a further or additional embodiment, the individual afflicted with prostate cancer (of step (e)) is not afflicted with any other prostate-related disorder. Preferably, the individual afflicted with prostate cancer is not afflicted with any other disease or condition. Most preferably, the individual afflicted with prostate cancer is an otherwise healthy individual. In one embodiment, the individual afflicted with prostate cancer is afflicted with group A, group B, group C, group C1, subgroup C1, subgroup C2 or subgroup D.

Preferably, step (e) comprises providing control samples from one or more individual from each of these groups, or any combination thereof.

In a further or additional embodiment step (b), (d) and/or step (f) is performed using a first binding agent capable of binding to the one or more biomarkers.

Preferably the first binding agent comprises or consists of an antibody or an antigen-binding fragment thereof.

The term "antibody" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecules capable of binding to an antigen in an immunoassay format that is known to those skilled in the art.

We also include the use of antibody-like binding agents, such as affibodies and aptamers.

A general review of the techniques involved in the synthesis of antibody fragments which retain their specific binding sites is to be found in Winter & Milstein (1991) *Nature* 349, 293-299.

Additionally, or alternatively, one or more of the first binding molecules may be an aptamer (see Collett et al., 2005, *Methods* 37:4-15).

Molecular libraries such as antibody libraries (Clackson et al, 1991, *Nature* 352, 624-628; Marks et al, 1991, *J Mol Biol* 222(3): 581-97), peptide libraries (Smith, 1985, *Science* 228(4705): 1315-7), expressed cDNA libraries (Santi et al (2000) *J Mol Biol* 296(2): 497-508), libraries on other scaffolds than the antibody framework such as affibodies (Gunneriusson et al, 1999, *Appl Environ Microbiol* 65(9): 4134-40) or libraries based on aptamers (Kenan et al, 1999, *Methods Mol Biol* 118, 217-31) may be used as a source from which binding molecules that are specific for a given motif are selected for use in the methods of the invention.

The molecular libraries may be expressed in vivo in prokaryotic cells (Clackson et al, 1991, op. cit.; Marks et al, 1991, op. cit.) or eukaryotic cells (Kieke et al, 1999, *Proc Natl Acad Sci USA*, 96(10):5651-6) or may be expressed in vitro without involvement of cells (Hanes & Pluckthun, 1997, *Proc Natl Acad Sci USA* 94(10):4937-42; He & Taussig, 1997, *Nucleic Acids Res* 25(24):5132-4; Nemoto et al, 1997, *FEBS Lett,* 414(2):405-8).

In cases when protein based libraries are used, the genes encoding the libraries of potential binding molecules are often packaged in viruses and the potential binding molecule displayed at the surface of the virus (Clackson et al, 1991, supra; Marks et al, 1991, supra; Smith, 1985, supra).

Perhaps the most commonly used display system is filamentous bacteriophage displaying antibody fragments at their surfaces, the antibody fragments being expressed as a fusion to the minor coat protein of the bacteriophage (Clackson et al, 1991, supra; Marks et al, 1991, supra). However, other suitable systems for display include using other viruses (EP 39578), bacteria (Gunneriusson et al, 1999, supra; Daugherty et al, 1998, *Protein Eng* 11(9):825-32; Daugherty et al, 1999, *Protein Eng* 12(7):613-21), and yeast (Shusta et al, 1999, *J Mol Biol* 292(5):949-56).

In addition, display systems have been developed utilising linkage of the polypeptide product to its encoding mRNA in so-called ribosome display systems (Hanes & Pluckthun, 1997, supra; He & Taussig, 1997, supra; Nemoto et al, 1997, supra), or alternatively linkage of the polypeptide product to the encoding DNA (see U.S. Pat. No. 5,856,090 and WO 98/37186).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

The antibody or antigen-binding fragment may be selected from the group consisting of intact antibodies, Fv fragments (e.g. single chain Fv and disulphide-bonded Fv), Fab-like fragments (e.g. Fab fragments, Fab' fragments and F(ab)2 fragments), single variable domains (e.g. $V_H$ and $V_L$ domains) and domain antibodies (dAbs, including single and dual formats [i.e. dAb-linker-dAb]). Preferably, the antibody or antigen-binding fragment is a single chain Fv (scFv).

The one or more binding moieties may alternatively comprise or consist of an antibody-like binding agent, for example an affibody or aptamer.

By "scFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli,* thus allowing the facile production of large amounts of the said fragments.

Whole antibodies, and F(ab')2 fragments are "bivalent". By "bivalent" we mean that the said antibodies and F(ab')2 fragments have two antigen combining sites. In contrast, Fab, Fv, ScFv and dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

When potential binding molecules are selected from libraries, one or more selector peptides having defined motifs are usually employed. Amino acid residues that provide structure, decreasing flexibility in the peptide or charged, polar or hydrophobic side chains allowing interaction with the binding molecule may be used in the design of motifs for selector peptides. For example:

(i) Proline may stabilise a peptide structure as its side chain is bound both to the alpha carbon as well as the nitrogen;

(ii) Phenylalanine, tyrosine and tryptophan have aromatic side chains and are highly hydrophobic, whereas leucine and isoleucine have aliphatic side chains and are also hydrophobic;
(iii) Lysine, arginine and histidine have basic side chains and will be positively charged at neutral pH, whereas aspartate and glutamate have acidic side chains and will be negatively charged at neutral pH;
(iv) Asparagine and glutamine are neutral at neutral pH but contain a amide group which may participate in hydrogen bonds;
(v) Serine, threonine and tyrosine side chains contain hydroxyl groups, which may participate in hydrogen bonds.

Typically, selection of binding molecules may involve the use of array technologies and systems to analyse binding to spots corresponding to types of binding molecules.

Hence, first binding agent may be, for example, a recombinant antibody or antigen-binding fragment thereof. Preferably, the antibody or antigen-binding fragment thereof is selected from the group consisting of: scFv; Fab; a binding domain of an immunoglobulin molecule.

The first binding agent may be immobilised on a surface.

Optionally, the one or more biomarkers in the test sample are labelled with a detectable moiety. The one or more biomarkers in the control sample(s) may alternatively or additionally labelled with a detectable moiety.

By a "detectable moiety" we include a moiety which permits its presence and/or relative amount and/or location (for example, the location on an array) to be determined, either directly or indirectly.

Suitable detectable moieties are well known in the art.

For example, the detectable moiety may be a fluorescent and/or luminescent and/or chemiluminescent moiety which, when exposed to specific conditions, may be detected. Such a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

Preferably, the detectable moiety is selected from the group consisting of: a fluorescent moiety; a luminescent moiety; a chemiluminescent moiety; a radioactive moiety; an enzymatic moiety. Most preferably the detectable moiety is biotin.

Clearly, the agent to be detected (such as, for example, the one or more biomarkers in the test sample and/or control sample described herein and/or an antibody molecule for use in detecting a selected protein) must have sufficient of the appropriate atomic isotopes in order for the detectable moiety to be readily detectable.

In a further or additional embodiment step (b), (d) and/or step (f) is performed using an assay comprising a second binding agent capable of binding to the one or more biomarkers, the second binding agent comprising a detectable moiety.

The radio- or other labels may be incorporated into the biomarkers present in the samples of the methods of the invention and/or the binding moieties of the invention in known ways. For example, if the binding agent is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57) can be used to incorporate $^{123}$I. Reference ("Monoclonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

It will be appreciated by persons skilled in the art that biomarkers in the sample(s) to be tested may be labelled with a moiety which indirectly assists with determining the presence, amount and/or location of said proteins. Thus, the moiety may constitute one component of a multicomponent detectable moiety. For example, the biomarkers in the sample(s) to be tested may be labelled with biotin, which allows their subsequent detection using streptavidin fused or otherwise joined to a detectable label.

Preferably the second binding agent comprises or consists of an antibody or an antigen-binding fragment thereof, for example, a recombinant antibody or antigen-binding fragment thereof. Preferably, the antibody or antigen-binding fragment thereof is selected from the group consisting of: scFv; Fab; a binding domain of an immunoglobulin molecule.

The one or more second binding agent(s) may be labelled with a detectable moiety, for example, the detectable moiety may be selected from the group consisting of: a fluorescent moiety; a luminescent moiety; a chemiluminescent moiety; a radioactive moiety; an enzymatic moiety. Preferably, the detectable moiety is fluorescent moiety (for example an Alexa Fluor dye, e.g. Alexa647).

In one embodiment of the first aspect of the invention the method comprises or consists of an ELISA (Enzyme Linked Immunosorbent Assay).

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides may be used in methods well known in cytology laboratory diagnostic tests, as well known to those skilled in the art.

Thus, in one embodiment the assay is an ELISA (Enzyme Linked Immunosorbent Assay) which typically involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemiluminescent systems based on enzymes such as luciferase can also be used.

Conjugation with the vitamin biotin is frequently used since this can readily be detected by its reaction with enzyme-linked avidin or streptavidin to which it binds with great specificity and affinity.

In an alternative embodiment, the assay used for protein detection is conveniently a fluorometric assay. Thus, the detectable moiety of the second binding agent may be a fluorescent moiety, such as an Alexa fluorophore (for example Alexa-647).

Preferably the predicative accuracy of the method, as determined by an ROC AUC value, is at least 0.50, for example at least 0.55, 0.60, 0.65, 0.70, 0.75, 0.80, 0.85, 0.90, 0.95, 0.96, 0.97, 0.98 or at least 0.99. More preferable the predicative accuracy of the method, as determined by an ROC AUC value, is at least 0.80 (most preferably 1).

In the method of the first aspect of the invention step (b) may be performed using an array such as a bead-based array or a surface-based array. Preferably the array is selected from the group consisting of: macroarray; microarray; nanoarray.

The method for determining a prostate cancer-associated disease state may be performed using a support vector machine (SVM), such as those available from http://cran.r-project.org/web/packages/e1071/index.html (e.g. e1071 1.5-24). However, any other suitable means may also be used. SVMs may also be used to determine the ROC AUCs of biomarker signatures comprising or consisting of one or more Table 1 biomarkers as defined herein.

Support vector machines (SVMs) are a set of related supervised learning methods used for classification and regression. Given a set of training examples, each marked as belonging to one of two categories, an SVM training algorithm builds a model that predicts whether a new example falls into one category or the other. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

More formally, a support vector machine constructs a hyperplane or set of hyperplanes in a high or infinite dimensional space, which can be used for classification, regression or other tasks. Intuitively, a good separation is achieved by the hyperplane that has the largest distance to the nearest training datapoints of any class (so-called functional margin), since in general the larger the margin the lower the generalization error of the classifier. For more information on SVMs, see for example, Burges, 1998, *Data Mining and Knowledge Discovery*, 2:121-167.

In one embodiment of the invention, the SVM is 'trained' prior to performing the methods of the invention using biomarker profiles of known agents (namely, prostate cancer cells of known histological grade or prostate cancer cells from prostate cancer patients with known distant metastasis-free survival). By running such training samples, the SVM is able to learn what biomarker profiles are associated with particular characteristics. Once the training process is complete, the SVM is then able whether or not the biomarker sample tested is from a particular prostate cancer sample type (i.e., a particular prostate cancer-associated disease state).

However, this training procedure can be by-passed by pre-programming the SVM with the necessary training parameters. For example, cells belonging to a particular prostate cancer-associated disease state can be identified according to the known SVM parameters using the measurement of the biomarkers listed in Table 1 and/or Table 2 using the values and/or regulation patterns detailed in the foregoing examples.

It will be appreciated by skilled persons that suitable SVM parameters can be determined for any combination of the biomarkers listed Table 1 and/or Table 2 by training an SVM machine with the appropriate selection of data (i.e. biomarker measurements from cells of known prostate cancer status, prostate cancer subtype status and/or known prostate cancer risk group).

Alternatively, the Table 1 and/or Table 2 data may be used to determine a particular prostate cancer-associated disease state according to any other suitable statistical method known in the art.

Preferably, the method of the invention has an accuracy of at least 65%, for example 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% accuracy.

Preferably, the method of the invention has a sensitivity of at least 65%, for example 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sensitivity.

Preferably, the method of the invention has a specificity of at least 65%, for example 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% specificity.

By "accuracy" we mean the proportion of correct outcomes of a method, by "sensitivity" we mean the proportion of all positive chemicals that are correctly classified as positives, and by "specificity" we mean the proportion of all negative chemicals that are correctly classified as negatives.

Alternatively or additionally, step (b), (d) and/or step (f) is performed using an array.

Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. Alternatively, affinity coupling of the probes via affinity-tags or similar constructs may be employed. By using well-known techniques, such as contact or non-contact printing, masking or photolithography, the location of each spot can be defined. For reviews see Jenkins, R. E., Pennington, S. R. (2001, *Proteomics*, 2, 13-29) and Lal et al (2002, *Drug Discov Today* 15; 7(18 Suppl):S143-9).

Typically the array is a microarray. By "microarray" we include the meaning of an array of regions having a density of discrete regions of at least about 100/cm$^2$, and preferably at least about 1000/cm$^2$. The regions in a microarray have typical dimensions, e.g. diameter, in the range of between about 10-250 μm, and are separated from other regions in the array by about the same distance. The array may alternatively be a macroarray or a nanoarray.

Once suitable binding molecules (discussed above) have been identified and isolated, the skilled person can manufacture an array using methods well known in the art of molecular biology; see Examples below.

The array may be a bead-based array but is preferably a surface-based array, for example, an arrays selected from the group consisting of: macroarray; microarray; and nanoarray.

However, the method may comprise:
(i) labelling biomarkers present in the sample with biotin;
(ii) contacting the biotin-labelled proteins with an array comprising a plurality of scFv immobilised at discrete locations on its surface, the scFv having specificity for one or more of the proteins in Table 1;
(iii) contacting the immobilised scFv with a streptavidin conjugate comprising a fluorescent dye; and
(iv) detecting the presence of the dye at discrete locations on the array surface wherein the expression of the dye on the array surface is indicative of the expression of a biomarker from Table 1 in the sample.

The method of the first aspect of the invention may comprise measuring in step (b), (d) and/or (f) the expression of a nucleic acid molecule encoding the one or more biomarkers.

Preferably the nucleic acid molecule is a cDNA molecule or an mRNA molecule (most preferably an mRNA molecule).

The expression of the one or more biomarker(s) in step (b), (d) and/or (f) may be performed using a method selected from the group consisting of Southern hybridisation, Northern hybridisation, polymerase chain reaction (PCR), reverse transcriptase PCR (RT-PCR), quantitative real-time PCR (qRT-PCR), nanoarray, microarray, macroarray, autoradiography and in situ hybridisation. Preferably, the expression of the one or more biomarker(s) in step (b) is determined using a DNA microarray.

Hence, measurement of the expression of the one or more biomarker(s) in step (b), (d) and/or (f) may be performed using one or more binding moieties, each individually capable of binding selectively to a nucleic acid molecule encoding one of the biomarkers identified in Table 1. The one or more binding moieties each comprise or consist of a nucleic acid molecule.

The one or more binding moieties may each comprise or consist of DNA, RNA, PNA, LNA, GNA, TNA or PMO (preferably DNA). Preferably the one or more binding moieties are 5 to 100 nucleotides in length (e.g., 15 to 35 nucleotides in length).

In one embodiment the binding moiety comprises a detectable moiety, for example, a detectable moiety selected from the group consisting of: a fluorescent moiety; a luminescent moiety; a chemiluminescent moiety; a radioactive moiety (for example, a radioactive atom); or an enzymatic moiety. Preferably the detectable moiety comprises or consists of a radioactive atom, for example, the radioactive atom may be selected from the group consisting of technetium-99m, iodine-123, iodine-125, iodine-131, indium-111, fluorine-19, carbon-13, nitrogen-15, oxygen-17, phosphorus-32, sulphur-35, deuterium, tritium, rhenium-186, rhenium-188 and yttrium-90.

However, the moiety may be a fluorescent moiety.

In one embodiment, the sample provided in step (b), (d) and/or (f) is selected from the group consisting of unfractionated blood, plasma, serum, tissue fluid, prostate tissue, prostate juice, bile and urine and is preferably selected from the group consisting of unfractionated blood, plasma and serum. Most preferably the sample provided in step (b), (d) and/or (f) is plasma.

A second aspect of the present invention provides an array for determining the presence of prostate cancer in an individual comprising one or more binding agent as defined in the first aspect of the invention or any embodiment or combination of embodiments thereof.

Preferably the array comprises one or more binding agent for each of the proteins defined in Table 1.

A third aspect of the present invention provides the use of one or more biomarkers selected from the group defined in the first aspect of the invention or any embodiment or combination of embodiments thereof as a prognostic and/or diagnostic marker.

Preferably the all of the biomarkers defined in Table 1 are used as a prognostic and/or diagnostic marker.

A fourth aspect of the present invention provides an isolated binding agent as defined in the first aspect of the invention or any embodiment or combination of embodiments thereof for use as a prognostic and/or diagnostic marker as defined the first aspect of the invention.

A fifth aspect of the present invention provides a kit for determining the presence of prostate cancer comprising:
A) one or more first binding agent as defined in the first aspect of the invention or any embodiment or combination of embodiments thereof, or an array according to the second aspect of the invention or any embodiment or combination of embodiments thereof; and
B) instructions for performing the method as defined in the first aspect of the invention or any embodiment or combination of embodiments thereof.

In one embodiment, the kit comprises a second binding agent as defined the first aspect of the invention or any embodiment or combination of embodiments thereof.

A sixth aspect of the present invention provides a method or use for determining the presence of prostate cancer-associated disease state in an individual substantially as described herein.

An array or kit for determining the presence of prostate cancer-associated disease state in an individual substantially as described herein.

Preferred, non-limiting examples which embody certain aspects of the invention will now be described with reference to the following figures and tables:

FIG. 1. Evaluation of recombinant scFv antibody microarray. A) Scanned image of a representative microarray containing 1440 data points (180 probes including controls×8 replicates). The image was scanned at 80% laser power and 80% PMT-gain. B) Intra-assay reproducibility, i.e. spot-to-spot variations. Data based on 162 different antibodies and 8 spot replicates. C) Inter-assay reproducibility, i.e. array-to-array variations. Data based on one sample analyzed on two independent arrays, each including 162 different antibodies.

Figure 2:
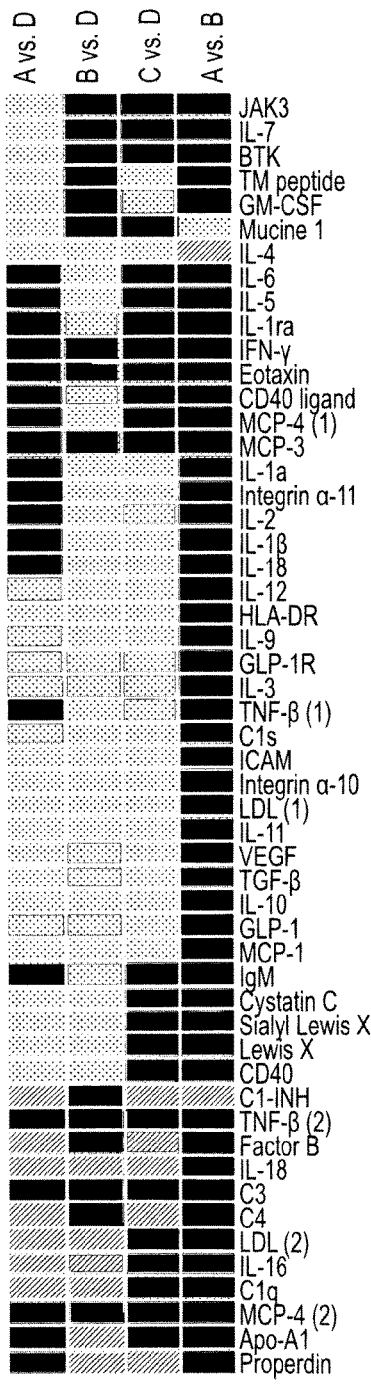
Figure 2:
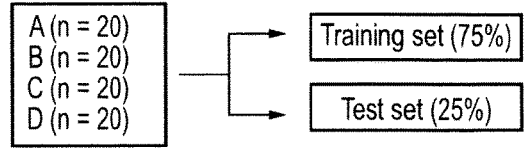
Figure 2:
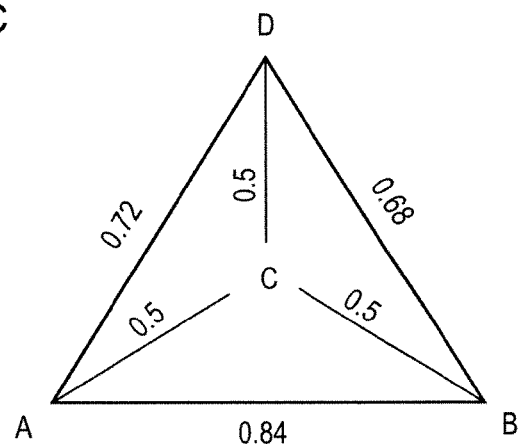

FIG. 2. Protein expression profiling of patient groups with increased risk of having PC. Four risk groups, denoted A (lowest risk) to D (highest risk), were á priori defined based on tPSA and % free PSA. A) Significantly differentially expressed analytes (p<0.05) were identified using Wilcoxon's signed-rank test and presented in heat maps; green—down-regulated, red—up-regulated, and black—equal levels. B) Each patient cohort was divided into a training set (75% of the samples) and a test set (25% of the samples). C) Classification of the patient cohorts A to D using an SVM based approach using all 162 antibodies, i.e. unfiltered data. The SVM model was trained on the training set and tested on the independent test set, and expressed in terms of ROC AUC values.

Figure 3:
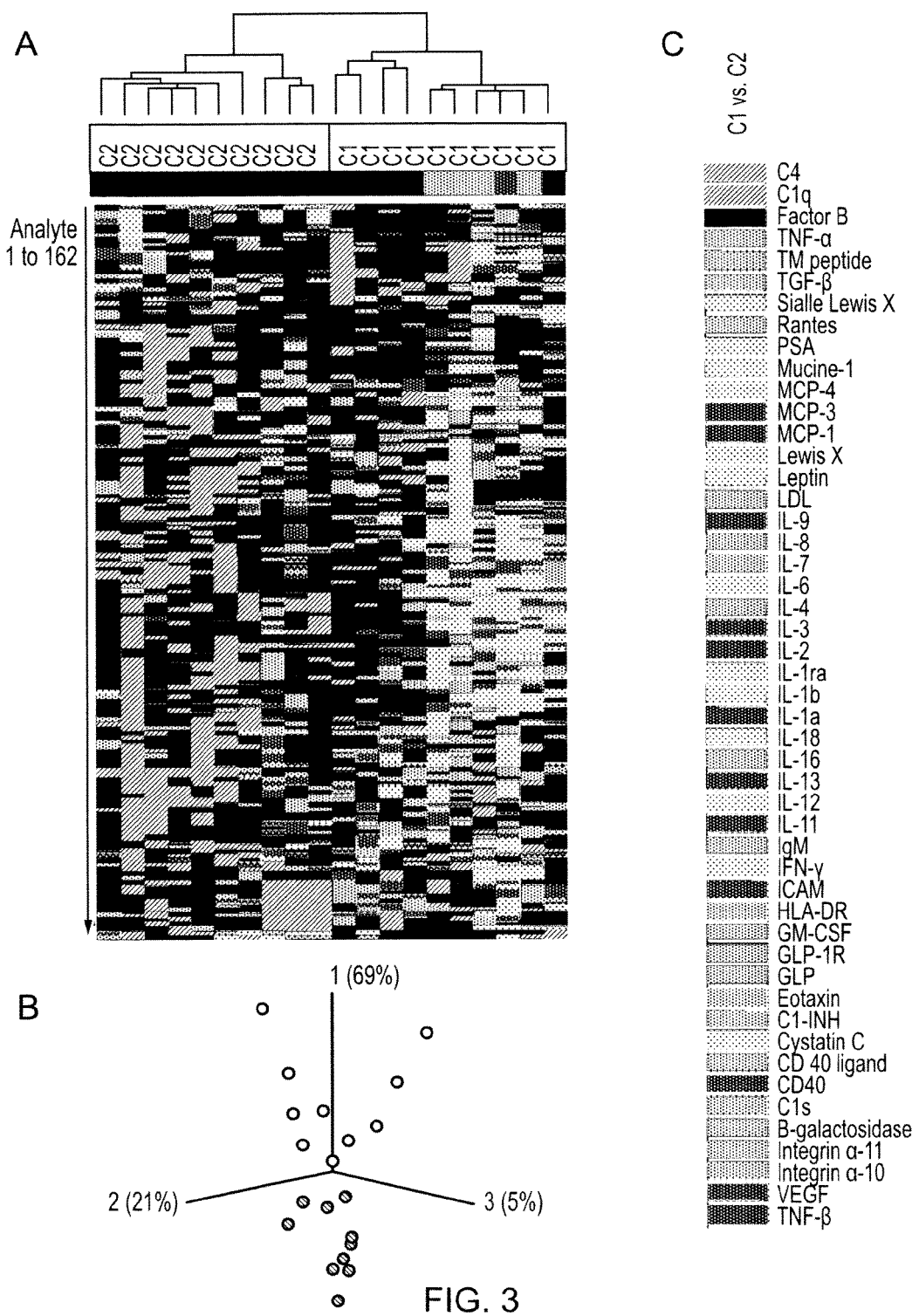
Figure 3:
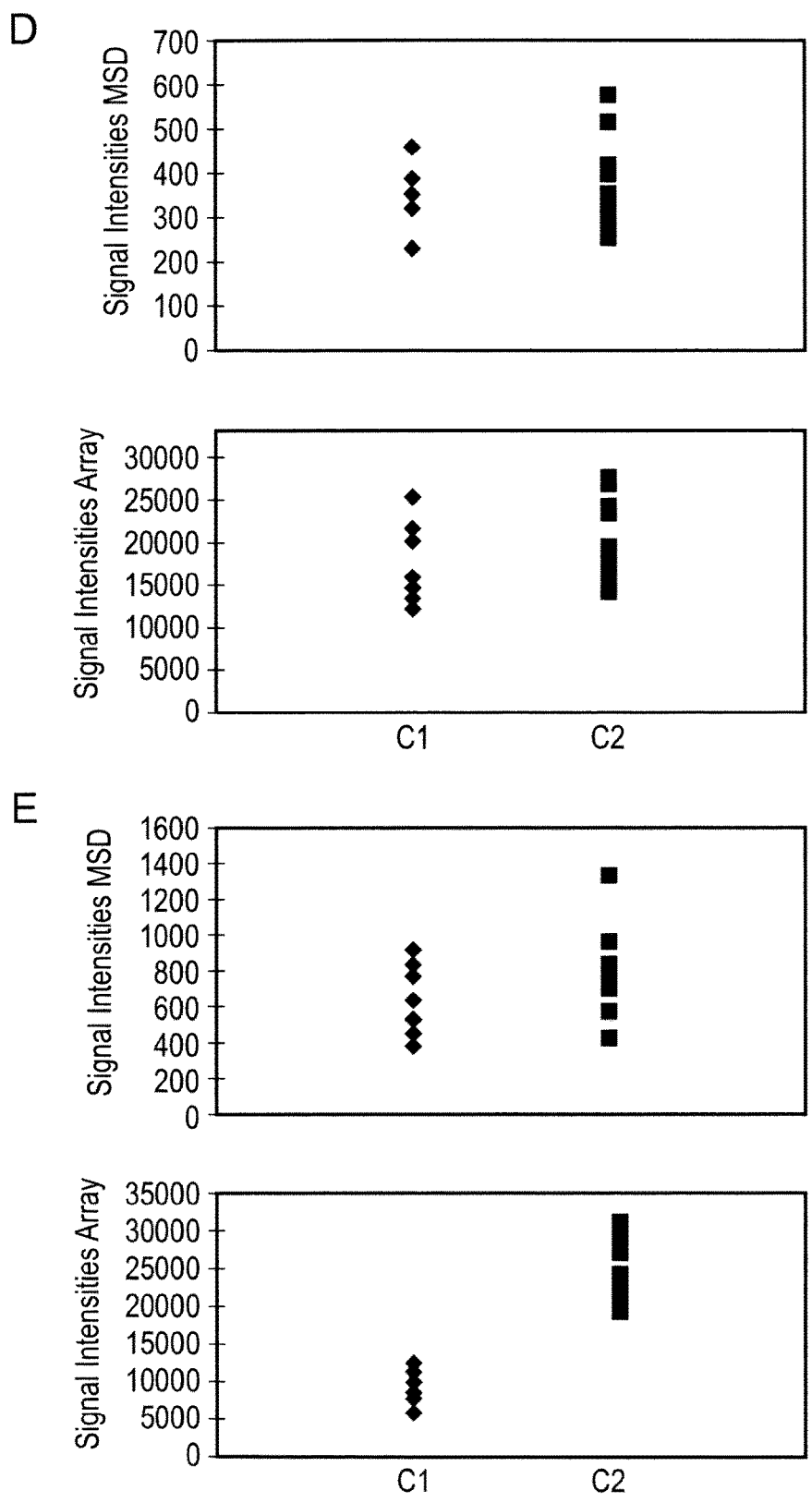

FIG. 3. Stratification of risk group C (mid-range tPSA and low % free PSA). A) Unsupervised hierarchical clustering based on all 162 antibodies, i.e. using unfiltered data, resulted in a division into two subgroups, denoted C1 (yellow) and C2 (Blue). B) Principle component analysis (PCA) based on unfiltered data, confirmed the stratification into subgroups C1 (yellow) and C2 (blue). C) Significantly differentially expressed analytes (p<0.05) were identified using Wilcoxon's signed-rank test and presented in heat maps; green—down-regulated, red—up-regulated and black—equal levels. D-E) Validation of the antibody microarray data of selected molecules using a 10-plex cytokine sandwich antibody assay (MSD). Data is only shown for those two analytes TNF-α (D) and IL-8 (E), for which a majority of the observed signals were above the lower limit of detection for the MSD assay. The MSD data is compared with the corresponding microarray data in those cases (C1 versus C2) where these two analytes were indicated to be differentially expressed.

Figure 4:
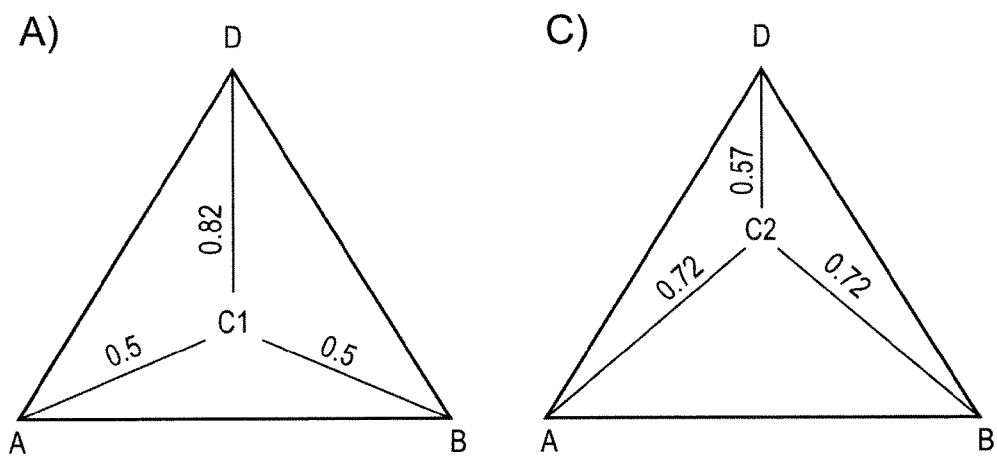
Figure 4:
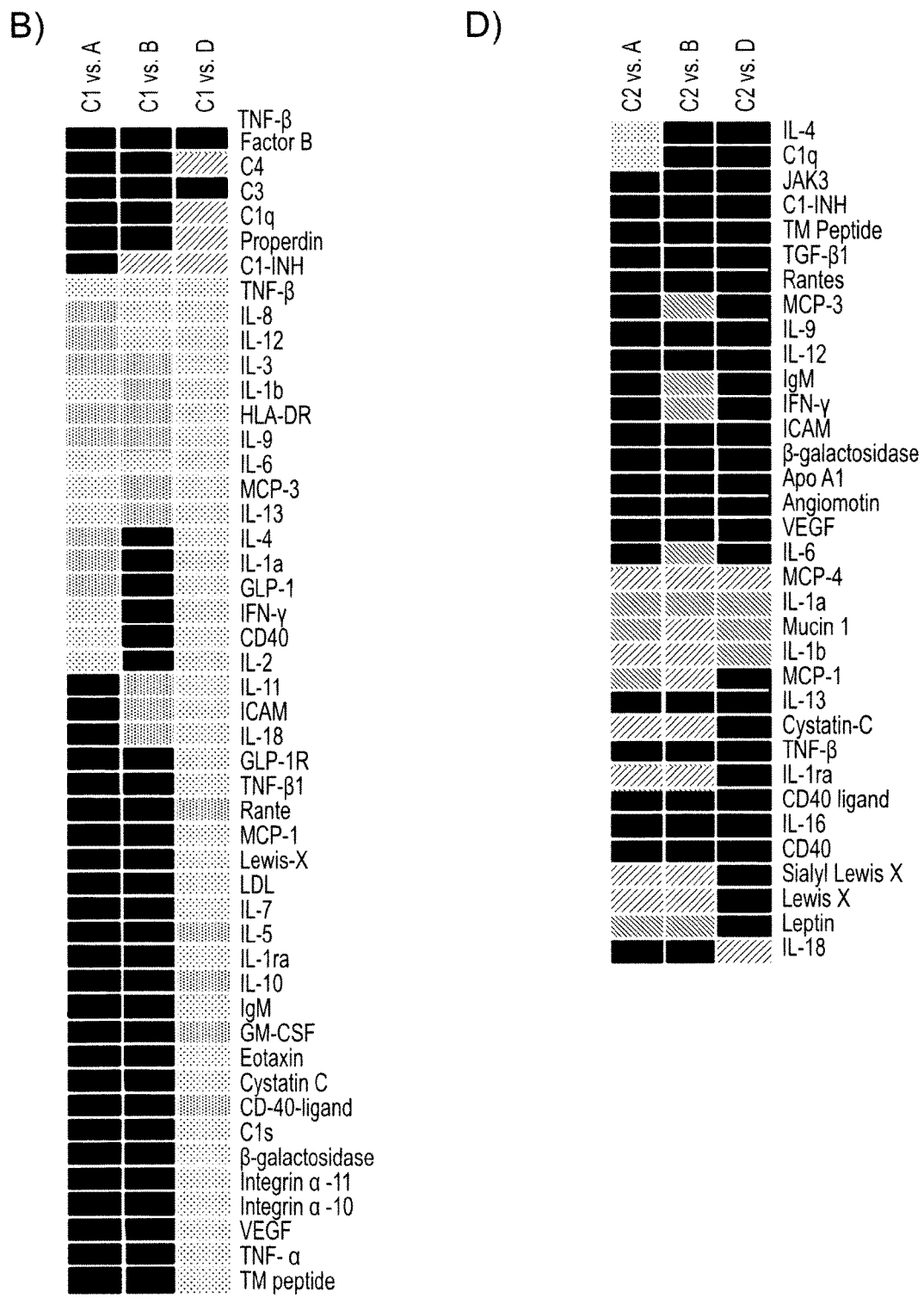
Figure 4:
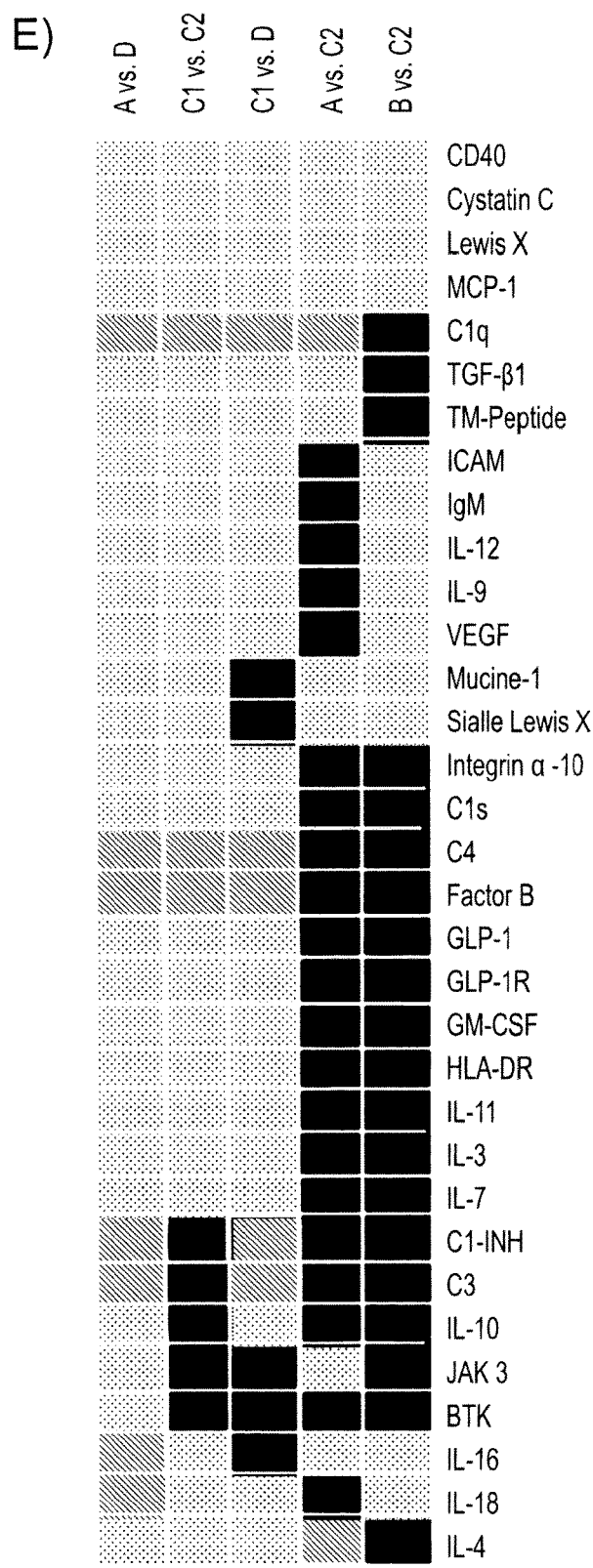

FIG. 4. Protein expression profiling of subgroups C1 and C2 versus the original risk groups A, B, and D. The samples were classified using a SVM-LOO cross-validation and ROC AUC-values were determined. Significantly differentially expressed biomarkers (p<0.05) were identified using Wilcoxon's signed-rank test, and presented in heat maps; red—up-regulated, green—down-regulated and black—equal levels. A) SVM-LOO cross-validation of C1 vs. A, B and D, respectively. B) Heat map displaying significantly differentially expressed analytes (p<0.05) for C1 versus A, B, and D, respectively. C) SVM-LOO cross-validation of C2 vs. A, B, and D, respectively. D) Heat map displaying significantly differently expressed analytes (p<0.05) for C2 versus A, B, and D respectively. E) Comparison of the malignant signature discriminating A versus D with the expression levels of the corresponding markers for C1 vs. C2, C1 vs. D, A vs. C2, and B vs. C2.

TABLE 1

BIOMARKERS FOR DETERMINING A PROSTATE CANCER-ASSOCIATED DISEASE STATE

| | No. | Biomarker | Accession No.(s) |
|---|---|---|---|
| A - core biomarkers | 1 | IL-4 | P05112 |
| | 2 | IL-12 | O60595 |
| | 3 | IL-9 | P15248 |
| | 4 | IL-1a | P01583 |
| B - preferred biomarkers | 5 | HLA-DR | HLA-DR is a MHC class II cell surface receptor encoded by the human leukocyte antigen complex on chromosome 6 region 6p21.31. |
| | 6 | IL-3 | P08700 |
| | 7 | ICAM | CAA41977.1, P05362 |
| | 8 | CD40 | Q6P2H9 |
| | 9 | IL-18 | Q14116 |
| | 10 | IL-1b | P01584 |

TABLE 1-continued

BIOMARKERS FOR DETERMINING A PROSTATE CANCER-ASSOCIATED DISEASE STATE

| | No. | Biomarker | Accession No.(s) |
|---|---|---|---|
| C - preferred biomarkers | 11 | GLP-1 | |
| | 12 | IL-11 | P20809 |
| | 13 | VEGF | P15692, P49765, P49767, =43915 |
| | 14 | Cystatin C | P01034 |
| | 15 | C1-INH | P05155 |
| | 16 | MCP-3 | BC112258, BC112260, BC092436, BC070240 |
| | 17 | IL-13 | P35225 |
| | 18 | TNF-β | P01374 |
| D - preferred biomarkers | 19 | C1s | P09871 |
| | 20 | Integrin α-10 | Hs158237 |
| | 21 | C3 | BC150179, BC150200; P01024 |
| | 22 | GLP-1R | P43220 |
| | 23 | IgM | e.g. P01871 (not complete protein); isotype-specific for IgM on Ramos B cells |
| | 24 | IL-16 | Q05BE6, Q8IUU6, B5TY35 |
| | 25 | TM peptide | NA |
| | 26 | Mucine-1 | P15941 |
| | 27 | IL-2 | P60568 |
| | 28 | IFN-γ | P01579 |
| | 29 | CD40 ligand | P29965 |
| E - preferred biomarkers | 30 | IL-10 | P22301 |
| | 31 | GM-CSF | P04141 |
| | 32 | Factor B | P00751 |
| | 33 | C4 | BC151204, BC146673, AY379959, AL645922, AY379927, AY379926, AY379925 |
| | 34 | Integrin α-11 | Q9UKX5 |
| | 35 | IL-8 | CR623827, CR623683, DQ893727, DQ890564, P10145 |
| | 36 | MCP-4 | Q99616 |
| | 37 | LDL (1) | |
| F - preferred biomarkers | 38 | TNF-β (1) | P01374 |
| | 39 | IL-7 | AK226000, AB102893, AB102885, P13232 |
| | 40 | Eotaxin | P51671 |
| | 41 | Rantes | P13501 |
| | 42 | β-galactosidase | P16278 |
| | 43 | Leptin | P41159 |
| | 44 | Mucin 1 | P15941 |
| | 45 | LDL (2) | |
| G - preferred biomarkers | 46 | JAK3 | P52333 |
| | 47 | IL-1β | P01584 |
| | 48 | Properdin | P27918 |
| | 49 | IL-5 | BC066282, CH471062, P05113 |
| | 50 | Apo-A1 | P02647 |
| | 51 | LDL | |
| | 52 | TNF-α | P01375 |
| | 53 | BTK | Q06187 |
| H - preferred biomarkers | 54 | TNF-β (2) | P01374 |
| | 55 | MCP-4 (1) | Q99616 |
| | 56 | MCP-4 (2) | Q99616 |
| | 57 | GLP | GLP-1R P43220 |
| | 58 | Angiomotin | AAG01851; Q4VCS5 |
| I - optional biomarkers | 59 | MCP-1 | P13500 |
| | 60 | IL-6 | P05231 |
| | 61 | Lewis X | |
| | 62 | C1q | IPR001073, PR00007 |
| | 63 | Sialyl Lewis X | |
| | 64 | TGF-β | P01137 |
| | 65 | IL-1ra | P18510 |
| | 66 | TGF-β1 | P01137 |
| | 67 | PSA | P07288 |

TABLE 2

BIOMARKER SUBSETS FOR DETERMINING A PROSTATE CANCER-ASSOCIATED DISEASE STATE

| | | A | B | C | D | E | F | G | H | I | J | K |
|---|---|---|---|---|---|---|---|---|---|---|---|---|
| | | | | | | INDICATIONS | | | | | | |
| | | AvD | BvD | CvD | AvB | C1vC2 | C1vA | C1vB | C1vD | C2vA | C2vB | C2vD |
| 1 | IL-4 | D | D | D | U | D | D | | D | D | | |
| 2 | IL-12 | D | D | D | | D | D | D | D | | U | |
| 3 | IL-9 | D | D | D | | D | D | D | D | | U | |
| 4 | IL-1a | | D | D | | D | D | | D | U | U | U |
| 5 | HLA-DR | D | D | D | | D | D | D | D | | | |
| 6 | IL-3 | D | D | D | | D | D | D | D | | | |
| 7 | ICAM | D | D | D | | D | | D | D | | U | |
| 8 | MCP-1 | D | D | D | | D | | | D | U | U | |
| 9 | CD40 | D | D | | | D | D | | D | U | U | |
| 10 | IL-18 | U | D | D | | D | | D | D | | U | U |
| 11 | IL-6 | | D | | | D | D | D | D | U | U | |
| 12 | IL-1b | | | | | D | D | D | D | U | U | U |
| 13 | GLP-1 | D | D | D | | D | D | | D | | | |
| 14 | IL-11 | D | D | D | | D | | D | D | | | |
| 15 | VEGF | D | D | D | | D | | | D | | U | |
| 16 | Cystatin C | D | D | | | D | | | D | U | U | |
| 17 | Lewis X | D | D | | | D | | | D | U | U | |
| 18 | C1-INH | U | | U | U | D | | | U | U | | |
| 19 | MCP-3 | | D | | | D | D | D | D | | U | |
| 20 | IL-13 | | | | | D | D | D | D | U | U | |
| 21 | TNF-β | | | | | D | D | D | D | U | U | |
| 22 | C1s | D | D | D | | D | | | D | | | |
| 23 | Integrin α-10 | D | D | D | | D | | | D | | | |
| 24 | C3 | U | U | U | | U | | | U | | | |
| 25 | GLP-1R | D | D | D | | D | | D | D | | | |
| 26 | C1q | U | U | | | U | | | U | D | | |
| 27 | IgM | D | D | | | D | | | D | | U | |
| 28 | IL-16 | U | U | | | D | | | | U | U | |
| 29 | Sialyl Lewis X | D | D | | | D | | | | U | U | |
| 30 | TM peptide | D | | D | | D | | | D | U | | |
| 31 | Mucine-1 | D | | | D | D | | | | D | D | |
| 32 | IL-2 | | D | D | | D | D | | D | | | |
| 33 | IFN-γ | | D | | | D | D | | D | | U | |
| 34 | CD40 ligand | | D | | | D | | | D | U | U | |
| 35 | IL-1ra | | D | | | D | | | D | U | U | |
| 36 | TGF-β | D | D | D | | D | | | | | | |
| 37 | IL-10 | D | D | D | | | | | D | | | |
| 38 | GM-CSF | D | | D | | D | | | D | | | |
| 39 | Factor B | U | | U | | U | | | U | | | |
| 40 | C4 | U | | U | | U | | | U | | | |
| 41 | TGF-β1 | D | | | | D | | | D | U | | |
| 42 | Integrin α-11 | | D | D | | D | | | D | | | |
| 43 | IL-8 | | | | | D | D | D | D | | | |
| 44 | MCP-4 | | | | | D | | | | U | U | U |
| 45 | LDL (1) | D | D | D | | | | | | | | |
| 46 | TNF-β (1) | D | D | D | | | | | | | | |
| 47 | IL-7 | D | | | | D | | | D | | | |
| 48 | Eotaxin | | D | | | D | | | D | | | |
| 49 | Rantes | | | | | D | | | D | | U | |
| 50 | β-galactosidase | | | | | D | | | D | | U | |
| 51 | Leptin | | | | | D | | | | U | U | |
| 52 | Mucin 1 | | | | | | | | | U | U | U |
| 53 | LDL (2) | U | U | | | | | | | | | |
| 54 | JAK3 | D | | | | | | | | U | | |
| 55 | IL-1β | | D | D | | | | | | | | |
| 56 | Properdin | | U | U | | | | | | | | |
| 57 | IL-5 | | D | | | | | | D | | U | |
| 58 | Apo-A1 | | U | | | | | | | | U | |
| 59 | LDL | | | | | D | | | D | | | |
| 60 | TNF-α | | | | | D | | | D | | | |
| 61 | BTK | D | | | | | | | | | | |
| 62 | TNF-β (2) | U | | | | | | | | | | |
| 63 | MCP-4 (1) | | D | | | | | | | | | |
| 64 | MCP-4 (2) | | U | | | | | | | | | |
| 65 | GLP | | | | | D | | | | | | |
| 66 | PSA | | | | | D | | | | | | |
| 67 | Angiomotin | | | | | | | | | | U | |

NB -
'D' = down-regulated; 'U' = up-regulated

TABLE 3

Clinical laboratory parameters of patient samples included in the study

| Group | Number of samples | tPSA (ng/ml) | % f PSA (free/total) |
|---|---|---|---|
| A | 20 | <0.70 | n/a[a] |
| B | 20 | 2.1-8.0 | ≥27.9% |
| C | 20 | 4-10 | ≤12.6% |
| D | 20 | 24.6-724 | n/a[a] |

[a]n/a = not applicable

TABLE 4

Summary of plasma biomarkers analyzed by the microarrays

Antigen (no. of clones)

Angiomotin (2)
Apolipoprotein A1(3)
β-galactosidase (1)
Bruton tyrosine kinase BTK (1)
C1 esterase inhibitor (4)
C1q (1)**
C1s (1)
C3 (6)**
C4 (4)**
C5 (3)**
CD40 (4)
CD40 ligand (1)
Choleratoxin subunit B (control) (1)
Cystatin C (4)
Digoxin (1)
Eotaxin (3)
Factor B (4)**
GLP-1 (1)
GLP-1-R (1)
GM-CSF (3)
HLA-DR (1)
ICAM (1)
IFN-γ (3)
IgM (4)
IL-1α (3)**
IL-1β (3)
IL-1-ra (3)
IL-2 (3)
IL-3 (3)
IL-4 (4)**
IL-5 (3)**
IL-6 (4)**
IL-7 (2)
IL-8 (3)*/**
IL-9 (3)
IL-10 (3)**
IL-11 (3)
IL-12 (4)**
IL-13 (3)**
IL-16 (3)
IL-18 (3)
Integrin α-10 (1)
Integrin α-11 (1)
LDL (2)
Leptin (1)
Lewis[x] (2)
Lewis[y] (1)
MCP-1 (8)**
MCP-3 (3)
MCP-4 (3)
Mucine-1 (6)
Procathepsin W (1)
Properdin (1)**
PSA (1)
Rantes (3)
Sialyl Lewis[x] (1)
TGF-β1 (3)
Tm peptide (1)
TNF-α (3)*

TABLE 4-continued

Summary of plasma biomarkers analyzed by the microarrays

Antigen (no. of clones)

TNF-β (4)**
Tyrosine-protein kinase JAK3 (1)
VEGF (4)**

*Antibody specificity determined by MSD.
**Antibody specificity previously validated by ELISA, MSD, protein array, blocking/spiking experiments, and/or mass spectrometry.

EXAMPLES

Introduction

Early detection of prostate cancer (PC) using prostate-specific antigen (PSA) in blood reduces PC-death among unscreened men. However, due to modest specificity of PSA at commonly used cut-offs, there are urgent needs for additional biomarkers contributing to enhanced risk classification among men with modestly elevated PSA. In this study, recombinant antibody microarrays were applied for protein expression profiling of 80 plasma samples from routine PSA-measurements, a priori divided into four risk groups, based on levels of total and % free PSA. The results demonstrated that plasma protein profiles could be identified that pin-pointed PC (a malignant biomarker signature) and most importantly that showed moderate to high correlation with biochemically defined PC risk groups. Notably, the data also implied that the risk group with mid-range PSA and low % free PSA, a priori known to be heterogeneous, could be further stratified into two subgroups, more resembling the lowest and highest risk groups, respectively. In conclusion, in this proof-of-concept study, we have thus shown that plasma protein biomarker signatures, associated with risk groups of PC, could be identified from crude plasma samples using affinity proteomics. This approach could in the longer perspective provide novel opportunities for improved risk classification of PC patients.

Material and Methods

Clinical Samples

We used de-identified EDTA anti-coagulated blood samples from 80 men aged 50-70 years referred for routinely performed PSA testing at the Dept. of Clinical Chemistry, Skåne University Hospital, Malmö, Sweden. No clinical information or patient identifiers were retained for these samples, and samples were stored at −80° C. until use (Table 3). The levels of free and tPSA were determined using the dual-label DELFIA Prostatus© total/free PSA-assay (Perkin-Elmer, Turku, Finland, which is calibrated against the WHO 96/670 (PSA-WHO) and WHO 68/668 (free PSA-WHO) calibrators. Detectable ranges were from 0.10 to 250 ng/ml for tPSA and from 0.04 to 250 ng/ml free PSA. Coefficients of variation (CV) for measuring tPSA was ≤10.6% for tPSA, and ≤7.3% for free PSA. The samples were divided into four groups based on the levels of % free and total PSA: A (n=20) had tPSA ≤0.70 ng/ml; B (n=20) had tPSA of 2.1-8.0 ng/ml with % fPSA ≥27.9%; C (n=20) had tPSA of 5.0-10-3 ng/ml with % fPSA ≤12.6%; and D (n=20) had tPSA of 24.6-724 ng/ml. These four groups of de-identified samples reflect highly different categories of risk of PC diagnosis or outcome with group A having very low long-term risk of significant PC, group B having modestly increased risk of prostate disease but low likelihood of clinically significant PC, group C with importantly increased risk of PC, and group D having very high risk of clinically significant or advanced stages of PC [38-41]. The procedures followed were in accordance with the Helsinki Declaration of 1975.

Labelling of Plasma Samples

EDTA anti-coagulated plasma samples were labeled according to a previously optimized protocol [28, 29] for serum proteomes with one minor adjustment. In order to prevent the plasma samples from coagulating, EDTA was added to a final concentration of 4 mM to the PBS buffers used throughout the protocol. Briefly, the samples were centrifuged at 16 000×g for 20 minutes at 4° C., and 5 µl of the samples were then diluted 45 times in 4 mM EDTA PBS, resulting in a total protein concentration of about 2 mg/ml. Diluted samples were incubated with 0.6 mM EZ-Link Sulfo-NHS-LC-Biotin (Pierce, Rockford, Ill., USA) for 2 hours on ice, after which unreacted biotin was removed by dialysis against 4 mM EDTA-PBS for 72 h at 4° C. Finally, samples were aliquoted and stored at −20° C. prior to use in microarray experiments.

Production and Purification of scFv

One hundred sixty-two human recombinant scFv antibody fragments directed against 62 different analytes, mainly involved in immunoregulation, were selected from the n-CoDeR library [42], and kindly provided by Bioinvent International AB (157 scFv clones; Lund, Sweden) and Prof. M. Ohlin (5 Mucine-1 specific clones; Dept. of Immunotechnology, Lund University, Lund, Sweden) (Supporting Information Table 3). The specificity, affinity (in the 1-10 nM range), and on-chip functionality of these phage-display derived scFv antibodies was ensured by using (i) stringent phage-display selection protocols [42], (ii) multiple clones (≤4) per target analyte and (iii) a molecular design adapted for microarray applications [26, 27]. In addition, the specificity/reactivity pattern of several of the antibodies have previously been validated using well-characterized serum samples, and orthogonal methods, such as ELISA, Meso Scale Discovery (MSD), cytometric bead array (CBA) and mass-spectrometry (MS), as well as using spiking and blocking experiments (Supporting Information Table 3) [31, 33, 34, 36]. All scFvs were produced in 100 ml E. coli cultures and purified from expression supernatants using affinity chromatography on $Ni^{2+}$-NTA Agarose (Qiagen, Hilden, Germany). Bound molecules were eluted with 250 mM Imidazole (Saveen Werner, Malmö, Sweden), dialysed against PBS, and then stored at 4° C. prior to use in microarray experiments. The integrity and purity of the scFvs were evaluated by 10% SDS-PAGE (Invitrogen, Carlsbad, Calif., USA). The protein concentration was determined by measuring the absorbance at 280 nm.

Production and Processing of Antibody Microarrays

Briefly, scFv microarrays were produced using a non-contact dispenser (SciFlexarrayer S11, Scienion, Berlin, Germany) and processed according to a set-up previously optimized [28, 29]. In total, 180 scFvs and controls were arrayed in 8 replicates onto Blank Polymer Maxisorp slides (NUNC A/S, Roskilde, Denmark), with one drop (300 pL) in each position, at a scFv concentration of 0.05-0.4 mg/ml. The 180 probes were arrayed into three columns, each comprising of 60 rows (FIG. 1A). AlexaFlour-647 labeled streptavidin (10 ug/ml) was printed as a position control, and printing buffer (PBS) was included as a negative control. After printing, the slides were allowed to dry and blocked in 5% (w/v) fat-free milk (Semper AB, Sundbyberg, Sweden) in PBS o/n. The slides were then placed in a Protein Array Workstation (Perkin Elmer Life & Analytical Sciences, Wellesley, Mass., USA) and washed for four minutes with 0.5% (w/v) Tween-20 in PBS (PBS-T). Next, 70 µl of the labeled samples, diluted 1:2 in 1% (w/v) fat-free milk powder and 1% (v/v) Tween-20 in PBS (PBS-MT), were injected and incubated with agitation for 60 minutes. After a second wash, the arrays where incubated for 60 minutes with 350 µl of 1 µg/ml Alexa-647 conjugated streptavidin in PBS-MT. After washing, the arrays were dried under a stream of nitrogen gas and scanned with a confocal microarray scanner (ScanArray Express, Perkin Elmer Life & Analytical Sciences) at 5 µm resolution, using five different scanner settings (50% PMT gain and 70% laser power (50/70), 70/70, 80/80, 80/90, and 90/90). Signal intensities were quantified using the ScanArray Express software version 4.0 (Perkin Elmer Life & Analytical Sciences). The local background was subtracted, and to compensate for any possible local defects, the two highest and lowest replicates were automatically excluded. Presented signal intensities represent the mean value for the remaining four replicate spots. Only unsaturated spots were considered for analysis Microarray Data Normalization Chip-to-chip normalization of the data sets was performed, using a semi-global normalization approach [32, 33], similar to the normalization developed for DNA microarrays. The coefficient of variation (CV) was first calculated for each analyte and ranked. The fifteen percent of the analytes that displayed the lowest CV-values over all samples were identified, corresponding to 24 analytes, and used to calculate a chip-to-chip normalization factor for each sample. The normalization factor Ni was calculated by the formula $Ni=Si/\mu$, where Si is the sum of the signal intensities for the 24 analytes for each sample and i is the sum of the signal intensities for the 24 analytes averaged over all samples. Each data set generated from one sample was divided with the normalization factor Ni. Log 2 values of signal intensities were used for further analyses.

Data Analysis

The 80 patient samples were divided into four groups (n=20) based on values of tPSA and % fPSA. For the initial classification analysis, each of the four risk groups was divided into a training set (n=15) and a test set (n=5). In order to classify the samples, we used the support vector machine (SVM), a supervised learning method in R [43]. The supervised classification was performed using a linear kernel, and the cost of constraints was set to 1, which is the default value in the R function SVM, and no attempt was performed to tune it in order to avoid overfitting. The SVM model was trained using the training set and then frozen, and applied to the test set. No filtration of the data was performed before training the SVM, i.e. data from all antibodies on the array were included in the analysis. Further, a receiver operating characteristics (ROC) curve, was constructed using the SVM decision values, and the area under the curve (AUC) was calculated. Using unsupervised hierarchical clustering in Cluster and Treeview [44], the C group could be divided into two subgroups denoted C1 (n=10) and C2 (n=10). Due to the smaller sample number, a division into training and test sets was in this case not possible, and the SVM was therefore trained using a leave-one-out cross-validation procedure. Significantly up- or down-regulated plasma proteins (p<0.05) were defined based on the relative protein levels and identified using Wilcoxon's signed-rank test. The samples were visualized using a principle component analysis (PC) software program (Qlucore Omics Explorer, Lund, Sweden) and/or Cluster and Treeview.

Validation Experiments

In an attempt to validate the antibody microarray results, a human Th1/Th2 10-plex MSD (Meso Scale Discovery, Gaithersburg, Md., USA) assay was run on all 80 EDTA-plasma samples. Each well of the MSD 96-plate had been pre-functionalized with antibodies against IFN-ã, IL-â, IL-2, IL-4, IL-5, IL-8, IL-10, IL-12p70, IL-13 and TNF-á in spatially distinct electrode spots. The assay was run according to the protocol provided by the manufacturer and the electrochemiluminiscence-based readout was performed in an MSD SECTOR® instrument. The limit of detection was defined as a signal 2.5 times the standard deviation over the zero point in the standard curve.

Results

In this study, we have performed protein expression profiling of non-fractionated, biotinylated EDTA-plasma samples from 80 patients at various levels of risk of having PC, using our in-house developed recombinant antibody microarrays. The samples had been a priori divided into four risk groups based on tPSA and % fPSA reflecting different categories of risk of PC diagnosis or outcome (Table 3).

Evaluation of scFv Microarray

A representative microarray image is shown in FIG. 1A, demonstrating that homogenous spot morphologies, high signal-to-noise ratios, and dynamic signal intensities were obtained. All 80 samples were successfully profiled; hence, array data from all 80 samples could be used for the subsequent statistical analysis. The intra-assay reproducibility was assessed by analyzing the spot-to-spot variation, resulting in an average coefficient of determination (R2) of 0.95 (FIG. 1B). The inter-assay reproducibility, i.e. array-to-array variation, was evaluated by analyzing a single sample on independent arrays, resulting in an R2-value of 0.96 (FIG. 1C).

Classification of Risk Groups

First, we determined a focused (62 analyte) plasma proteome profile of the four prostate cancer risk groups, denoted A-D (Table 3), with group A displaying the lowest risk and group D the highest risk. Using Wilcoxon's signed-rank test, 3 to 44 differentially expressed (p<0.05) plasma analytes were identified, which are shown as a heat map in FIG. 2A. The data showed that only 3 analytes were differently expressed between the two lowest risk groups, A and B. Hence, as could be expected from a clinical point of view, the data implied only small differences between the two lowest risk groups. In contrast, 37, 44, and 30 de-regulated analytes were observed for groups A, B, or C versus the highest risk group D, indicating at large(r) differences. In more detail, several complement proteins (e.g. C3, C4, C1q, Factor B and Properdine) were found to be down-regulated in the high risk group D, while the up-regulated analytes displayed a complex pattern of both TH1 (e.g. IL-2, IL-3 and INF-a) and TH2 (e.g. IL-4, IL-10) cytokines. Most importantly, the biomarker signature differentiating group A (very low PC-risk) versus group D (very high risk of clinically significant or advanced stages of PC) could be viewed as a malignant biomarker signature pin-pointing PC.

Next, we evaluated the ability of the array platform to classify the four risk groups (A to D), based on the observed protein expression profiles. To this end, each patient group was divided into a training set (75% of the samples) and a test set (25% of the samples) (FIG. 2B). Hence, the SVM model was trained on the training set and then applied on the independent test set. The results showed that the risk groups could be distinguished with different accuracy, with groups B and D displaying an AUC of 0.68, groups A and B an AUC of 0.84 (based on three analytes only), and groups A and D an AUC of 0.72 (FIG. 2C). Thus, the data showed that malignant signature could be used to well discriminate group A (very low risk) versus group D (very high risk of clinically significant or advanced stages of PC) (cfs. FIGS. 2A and 2C). In contrast, the C group could not be differentiated from any of the three other risk groups (AUC=0.5 in all cases). In this context, it should be noted that the C group represents a heterogeneous patient group (mid-range tPSA, low % free PSA) of which only 25-50% actually have PC, although all are selected for biopsy testing. Hence, stratification of this heterogeneous patient group could potentially be a key instrument for identifying patients at higher or lower risk of developing PC.

Stratification of Risk Group C

In order to investigate whether the C risk group could be further stratified, we performed an unsupervised hierarchical clustering based on unfiltered data, i.e. using data from all antibodies included on the array. The result showed that the C risk group could indeed be stratified into two distinct subgroups, denoted C1 and C2 (FIG. 3A). Similarly, a clear subdivision of the C cohort was also observed, using principle component analysis (PCA), (FIG. 3B). Moreover, 49 significantly differentially (p<0.05) expressed plasma analytes were observed for C1 versus C2 (FIG. 3C). In more detail, three complement proteins were up-regulated in C1 (C1q, Factor B and C4), while the remaining differentially expressed proteins were down-regulated in C1. The latter group of analytes included a number of cytokines (e.g. IL-6 and IL-4), complement proteins (e.g. C1-INH and C1s), as well as cell surface proteins (e.g. ICAM, HLA-DR, Mucine-1 and CD-40). Taken together, the data showed that the heterogeneous risk group C could be stratified into two distinct subgroups, C1 and C2, with a large number of deregulated analytes.

To validate the array data, an independent 10-plex cytokine sandwich antibody microarray (MSD) was applied (FIGS. 3D and 3E). The observed down-regulation of TNF-α (FIG. 3D) and IL-8 (IL-8) (FIG. 3E) in C1 versus C2 could be validated by the MSD data.

Risk classification of subgroups C1 and C2

In order to assess the biological impact of the stratified subdivision of risk group C, the protein expression profiles of subgroups C1 and C2 were compared to those of the other three original risk groups, A, B and D. In case of C1, the results showed that C1 could be well differentiated from risk group D (AUC=0.82), but not from risk groups A and B (AUC=0.5 in both cases) (FIG. 4A). Furthermore, 47 differentially expressed analytes were observed for C1 versus D, but only 16 and 15 for C1 versus A and B, respectively (FIG. 4B). In the former case, a pattern of up-regulated complement proteins (e.g. C1q, C3, and Factor B) and down regulated cytokines (e.g. TGF-â1, IL-1ra, IL-6 and MCP-1) and cell surface markers (e.g. ICAM, CD40 and LewisX) were observed in C1 versus D.

In contrast, the results showed that C2 could be well differentiated from both risk group A (AUC=0.72) and B (AUC=0.75), but not from risk group D (AUC=0.57 (FIG. 4C). In this case, 22 and 28 de-regulated analytes were observed for C2 versus A and B, respectively, but only 5 for C2 versus D (FIG. 4D). While only two down-regulated analytes (C1q and IL-4) were observed in C2 versus A, a pattern of up-regulated cytokines (e.g. IL-1ra, MCP-1, and IL-6) and cell surface markers (e.g. CD40, LewisX and Sialyl LewisX) were observed in C2 versus both A and B. Taken together, the results showed that C1 was more similar to the lowest risk groups A and B, while C2 displayed a higher similarity to the highest risk group D, indicating that the C1 group represented low risk patients and the C2 group high risk patients.

Finally, to further highlight the biological relevance, we compared the overlap of the malignant signature (33 biomarkers) discriminating risk group A (very low risk) versus risk group D (very high risk of clinically significant or advanced stages of PC) (FIG. 2A) with the expression levels of the corresponding markers of the above signatures (FIG. 4E). The data showed that a significant part of the malignant biomarker signature was also differentially expressed in the case of C1 versus C2 (27 of 33 biomarkers) and C1 versus D (29 of 33 biomarkers), while the overlap was significant smaller with the signatures differentiating A versus C2 and B versus C2. Hence, the data further indicated the biological relevance of the malignant biomarker signature pin-pointing PC.

Discussion

Blood plasma is a minimally invasive and clinically well-established sample format that would be the ideal source of biomarkers for early detection and risk classification of PC. Consequently, it has also been assessed for this purpose in numerous large-scale proteomic efforts [19, 20]. However, due to the inherent complexity of plasma samples, with respect to number of proteins and dynamic range, it has been argued that classical proteomic analysis of non-fractionated samples would be unlikely to be useful for classifying PC [21]. Although pre-fractionation reduces the sample complexity, it has in turn been associated with serious issues regarding skewed protein yield/recovery, as well as reproducibility and sensitivity [22, 23]. In this context, we have recently shown that affinity proteomics, represented by recombinant antibody microarrays, could be used to profile high- as well as low-abundant analyst in crude proteomes [26, 27]. Previously, a single serum marker thrombospondin-1 (TSP-1), was shown to be able to differentiate between benign and malignant prostatic disease using antibody microarrays [45]. In this proof-of-concept study, we have used affinity proteomics targeting crude plasma samples in order to decipher the first multiplexed candidate plasma protein biomarker signatures associated with risk groups for PC. Hence, recombinant antibody microarray-based analysis of PC demonstrated a potential route toward defining the next generation of PC-associated biomarkers.

The blood plasma proteome consists of both classical plasma proteins, as well as tissue leakage proteins. The intrinsic ability of the human immune system to sense even subtle changes in the body's homeostasis, ranging from a bacterial infection to a growing tumor, provides a unique opportunity of using the immune system as a remote and early sensor of disease [46]. In fact, immunosignaturing has gained significant interest [47], in particular due to recent studies showing immunosurveillance as an important factor in tumor development [48]. To this end, we have designed and applied a recombinant antibody microarray targeting mainly immunoregulatory analytes [26, 27]. Previously we have demonstrated the potential of our array design for cancer diagnosis [32, 33], evidence-based therapy selection [35], as well as predicting the risk for breast cancer recurrence [37]. In this discovery study, we have extended the range of applications, and indicated its potential use for risk group stratification in PC, clearly differentiating the two lowest versus the highest risk groups.

Risk classification of potential PC patients can currently be performed in the clinic, using serum PSA assays (tPSA and % free PSA) [49], one of a few models for risk classification [3, 50, 51]. Although this approach enables detection of many tumors, the low specificity for malignant disease results in several patients being subjected to unnecessary biopsy testing [3]. This number could be significantly decreased if the clinicians had access to more adequate tools for risk classification. In particular, the patient group with mid-range tPSA (4-10 ng/ml) and low % fPSA is known to be heterogeneous, including a mix of PC and benign prostatic hyperplasia [7, 49]. In our attempt to classify the four pre-determined risk groups, the results showed in fact that the patient groups with mid-range tPSA and low % fPSA (group C) could not be differentiated from any of the other three risk groups. Hence, our data further supported the current notion of group C being a very heterogeneous patient group.

However, our data rather implied that the C group could be divided into two distinct subgroups, C1 and C2, which, as anticipated from the current literature [2, 3, 5, 49], more resembled the two lowest and the highest original risk groups, respectively. When aiming for personalized treatment of cancer patients, the ability to stratify heterogeneous patient groups into more accurate subgroups of higher and lower risk of having (developing) a certain cancer will be instrumental. In the long run, this could provide novel opportunities for managing PC cancer patients. However, this discovery study was in part limited by the fact that full clinical documentation of the patients included was not at hand, and the observed candidate biomarker signatures will be properly validated in follow-up studies, targeting larger, independent cohorts of well-characterized patients. Notably, the two cytokines, IL-6 and TNF-á, that could be detected with the orthogonal method (MSD) used for initial validation, supported our discrimination of C1 versus C2.

When examining the candidate biomarker signatures in more detail, novel as well as a number of biologically relevant analytes already known to reflect high and low risk of PC were observed. Briefly, TGF-a1 has been shown to be associated with PC, e.g. promoting cell progression in PC models, higher tumor grade, and metastasis, and has subsequently been proposed as a tentative biomarker [3, 4, 52]. Accordingly, we found TGF-a1 to be down-regulated in the two lowest risk groups, A and B, versus the highest risk group, D. In addition, it was also down-regulated in A and B versus C2 (high risk), C1 (low risk) versus D, as well as in C1 versus C2. In the case of IL-6, this cytokine has also been suggested as a potential biomarker for PC [3, 4]. Our data showed that IL-6 was down-regulated in the various comparisons of the low risk groups (A, B, or C1) versus the high risk groups (D or C2), respectively. Furthermore, other cytokines known to be down-regulated in the low risk groups, such as IL-1ra and MCP-1 [53, 54], was also found to be down regulated in the different comparisons of the low risk groups (A, B or C1) versus the high risk groups (D or C2), further supporting our reported observations. In addition, the observation that Lewis X was down-regulated in the low risk groups was in accordance with previous results, indicating Lewis X as a prognostic parameter in prostate cancer [55]. It should be noted these observations also supported the candidate malignant biomarker signature observed to pinpoint PC. To date, complement proteins have not been significantly reported in the context of PC. Our data showed that different combinations of several complement proteins, such as C1q, C3, C4, properdin, and/or C1-INH, were up-regulated in the various low risk groups versus the high risk groups, respectively. Although previously not reported in clinical studies, C1q has been shown to display a protective role in prostate cancer cell lines [56].

Taken together, we have delineated candidate plasma biomarker signatures associated with PC risk groups as well as PC using affinity proteomics. Targeting independent patient cohorts, the results indicated that the conventional risk groups, a priori defined based on clinical parameters

REFERENCES

[1] Ferlay, J., Shin, H. R., Bray, F., Forman, D., et al., Estimates of worldwide burden of cancer in 2008: GLOBOCAN 2008. *Int J Cancer* 2010, 127, 2893-2917.

[2] Parekh, D. J., Ankerst, D. P., Troyer, D., Srivastava, S., Thompson, I. M., Biomarkers for prostate cancer detection. *J Urol* 2007, 178, 2252-2259.

[3] Shariat, S. F., Semjonow, A., Lilja, H., Savage, C., et al., Tumor markers in prostate cancer I: blood-based markers. *Acta Oncol* 2011, 50 Suppl 1, 61-75.

[4] Steuber, T., O'Brien, M. F., Lilja, H., Serum markers for prostate cancer: a rational approach to the literature. *Eur Urol* 2008, 54, 31-40.

[5] Catalona, W. J., Partin, A. W., Slawin, K. M., Brawer, M. K., et al., Use of the percentage of free prostate-specific antigen to enhance differentiation of prostate cancer from benign prostatic disease: a prospective multicenter clinical trial. *Jama* 1998, 279, 1542-1547.

[6] Bjork, T., Lilja, H., Christensson, A., The prognostic value of different forms of prostate specific antigen and their ratios in patients with prostate cancer. *BJU Int* 1999, 84, 1021-1027.

[7] Gann, P. H., Ma, J., Catalona, W. J., Stampfer, M. J., Strategies combining total and percent free prostate specific antigen for detecting prostate cancer: a prospective evaluation. *J Urol* 2002, 167, 2427-2434.

[8] *Cancer Diagnostic Testing World Markets*, TriMark Publications, LLC 2008.

[9] Vickers, A. J., Cronin, A. M., Aus, G., Pihl, C. G., et al., A panel of kallikrein markers can reduce unnecessary biopsy for prostate cancer: data from the European Randomized Study of Prostate Cancer Screening in Goteborg, Sweden. *BMC Med* 2008, 6, 19.

[10] Vickers, A. J., Gupta, A., Savage, C. J., Pettersson, K., et al., A panel of kallikrein marker predicts prostate cancer in a large, population-based cohort followed for 15 years without screening. *Cancer Epidemiol Biomarkers Prev* 2011, 20, 255-261.

[11] Jansen, F. H., van Schaik, R. H., Kurstjens, J., Horninger, W., et al., Prostate-specific antigen (PSA) isoform p2PSA in combination with total PSA and free PSA improves diagnostic accuracy in prostate cancer detection. *Eur Urol* 2010, 57, 921-927.

[12] Stephan, C., Jung, K., Lein, M., Sinha, P., et al., Molecular forms of prostate-specific antigen and human kallikrein 2 as promising tools for early diagnosis of prostate cancer. *Cancer Epidemiol Biomarkers Prev* 2000, 9, 1133-1147.

[13] Becker, C., Piironen, T., Pettersson, K., Bjork, T., et al., Discrimination of men with prostate cancer from those with benign disease by measurements of human glandular kallikrein 2 (HK2) in serum. *J Urol* 2000, 163, 311-316.

[14] Piironen, T., Haese, A., Huland, H., Steuber, T., et al., Enhanced discrimination of benign from malignant prostatic disease by selective measurements of cleaved forms of urokinase receptor in serum. *Clin Chem* 2006, 52, 838-844.

[15] Thompson, T. C., Truong, L. D., Timme, T. L., Kadmon, D., et al., Transforming growth factor beta 1 as a biomarker for prostate cancer. *J Cell Biochem Suppl* 1992, 16H, 54-61.

[16] Shariat, S. F., Kaftan, M. W., Traxel, E., Andrews, B., et al., Association of pre- and postoperative plasma levels of transforming growth factor beta(1) and interleukin 6 and its soluble receptor with prostate cancer progression. *Clin Cancer Res* 2004, 10, 1992-1999.

[17] Hobisch, A., Eder, I. E., Putz, T., Horninger, W., et al., Interleukin-6 regulates prostate-specific protein expression in prostate carcinoma cells by activation of the androgen receptor. *Cancer Res* 1998, 58, 4640-4645.

[18] Nakashima, J., Tachibana, M., Horiguchi, Y., Oya, M., et al., Serum interleukin 6 as a prognostic factor in patients with prostate cancer. *Clin Cancer Res* 2000, 6, 2702-2706.

[19] Matharoo-Ball, B., Ball, G., Rees, R., Clinical proteomics: discovery of cancer biomarkers using mass spectrometry and bioinformatics approaches—a prostate cancer perspective. *Vaccine* 2007, 25 Suppl 2, B110-121.

[20] McLerran, D., Grizzle, W. E., Feng, Z., Thompson, I. M., et al., SELDI-TOF MS whole serum proteomic profiling with IMAC surface does not reliably detect prostate cancer. *Clin Chem* 2008, 54, 53-60.

[21] Goo, Y. A., Goodlett, D. R., Advances in proteomic prostate cancer biomarker discovery. *J Proteomics* 2010, 73, 1839-1850.

[22] Hanash, S., Disease proteomics. *Nature* 2003, 422, 226-232.

[23] Hu, S., Loo, J. A., Wong, D. T., Human body fluid proteome analysis. *Proteomics* 2006, 6, 6326-6353.

[24] Ramachandran, N., Srivastava, S., Labaer, J., Applications of protein microarrays for biomarker discovery. *Proteomics Clin Appl* 2008, 2, 1444-1459.

[25] Haab, B. B., Applications of antibody array platforms. *Curr Opin Biotechnol* 2006, 17, 415-421.

[26] Borrebaeck, C. A., Wingren, C., Design of high-density antibody microarrays for disease proteomics: key technological issues. *J Proteomics* 2009, 72, 928-935.

[27] Borrebaeck, C. A., Wingren, C., Recombinant antibodies for the generation of antibody arrays. *Methods Mol Biol* 2011, 785, 247-262.

[28] Ingvarsson, J., Larsson, A., Sjoholm, A. G., Truedsson, L., et al., Design of recombinant antibody microarrays for serum protein profiling: targeting of complement proteins. *J Proteome Res* 2007, 6, 3527-3536.

[29] Wingren, C., Ingvarsson, J., Dexlin, L, Szul, D., Borrebaeck, C. A., Design of recombinant antibody microarrays for complex proteome analysis: choice of sample labeling-tag and solid support. *Proteomics* 2007, 7, 3055-3065.

[30] Dexlin-Mellby, L., Sandstrom, A., Antberg, L., Gunnarsson, J., et al., Design of recombinant antibody microarrays for membrane protein profiling of cell lysates and tissue extracts. *Proteomics* 2011, 11, 1550-1554.

[31] Kristensson, M., Olsson K., Carlson J., Wullt B., Sturfelt G., Borrebaeck C A K. and Wingren C., Design of Recombinant Antibody Microarrays for Urinary Proteomics. *Proteomics—Clinical Applications* 2012, In press.

[32] Carlsson, A., Wingren, C., Ingvarsson, J., Ellmark, P., et al., Serum proteome profiling of metastatic breast cancer using recombinant antibody microarrays. *Eur J Cancer* 2008, 44, 472-480.

[33] Ingvarsson, J., Wingren, C., Carlsson, A., Ellmark, P., et al., Detection of pancreatic cancer using antibody microarray-based serum protein profiling. *Proteomics* 2008, 8, 2211-2219.

[34] Dexlin-Mellby, L., Sandstrom, A., Centlow, M., Nygren, S., of al., Tissue proteome profiling of preeclamptic placenta using recombinant antibody microarrays. *Proteomics Clin Appl* 2010, 4, 794-807.

[35] Carlsson, A., Persson, O., Ingvarsson, J., Widegren, B., et al., Plasma proteome profiling reveals biomarker patterns associated with prognosis and therapy selection in glioblastoma multiforme patients. *Proteomics Clin Appl* 2010, 4, 591-602.

[36] Carlsson, A., Wuttge, D. M., Ingvarsson, J., Bengtsson, A. A., et al., Serum protein profiling of systemic lupus erythematosus and systemic sclerosis using recombinant antibody microarrays. *Mol Cell Proteomics* 2011, 10, M110 005033.

[37] Carlsson, A., Wingren, C., Kristensson, M., Rose, C., et al., Molecular serum portraits in patients with primary breast cancer predict the development of distant metastases. *Proc Natl Acad Sci USA* 2011, 108, 14252-14257.

[38] Lilja, H., Cronin, A. M., Dahlin, A., Manjer, J., et al., Prediction of significant prostate cancer diagnosed 20 to 30 years later with a single measure of prostate-specific antigen at or before age 50. *Cancer* 2011, 117, 1210-1219.

[39] Lilja, H., Ulmert, D., Vickers, A. J., Prostate-specific antigen and prostate cancer: prediction, detection and monitoring. *Nat Rev Cancer* 2008, 8, 268-278.

[40] Thompson, I. M., Pauler, D. K., Goodman, P. J., Tangen, C. M., et al., Prevalence of prostate cancer among men with a prostate-specific antigen level < or =4.0 ng per milliliter. *N Engl J Med* 2004, 350, 2239-2246.

[41] Vickers, A. J., Cronin, A. M., Bjork, T., Manjer, J., et al., Prostate specific antigen concentration at age 60 and death or metastasis from prostate cancer: case-control study. *BMJ* 2010, 341, c4521.

[42] Soderlind, E., Strandberg, L., Jirholt, P., Kobayashi, N., et al., Recombining germline-derived CDR sequences for creating diverse single-framework antibody libraries. *Nat Biotechnol* 2000, 18, 852-856.

[43] Ihaka R., R. G., R: A language for data analysis and graphics. *J Computational and Graphicla Statistics* 1996, 5, 299-314.

[44] Eisen, M. B., Spellman, P. T., Brown, P. O., Botstein, D., Cluster analysis and display of genome-wide expression patterns. *Proc Natl Acad Sci USA* 1998, 95, 14863-14868.

[45] Shafer, M. W., Mangold, L., Partin, A. W., Haab, B. B., Antibody array profiling reveals serum TSP-1 as a marker to distinguish benign from malignant prostatic disease. *Prostate* 2007, 67, 255-267.

[46] Tan, E. M., Zhang, J., Autoantibodies to tumor-associated antigens: reporters from the immune system. *Immunol Rev* 2008, 222, 328-340.

[47] Chaudhuri, D., Suriano, R., Mittelman, A., Tiwari, R. K., Targeting the immune system in cancer. *Curr Pharm Biotechnol* 2009, 10, 166-184.

[48] Chow, M. T., Moller, A., Smyth, M. J., Inflammation and immune surveillance in cancer. *Semin Cancer Biol* 2011.

[49] Shariat, S. F., Karam, J. A., Margulis, V., Karakiewicz, P. I., New blood-based biomarkers for the diagnosis, staging and prognosis of prostate cancer. *BJU Int* 2008, 101, 675-683.

[50] Bastian, P. J., Carter, B. H., Bjartell, A., Seitz, M., et al., Insignificant prostate cancer and active surveillance: from definition to clinical implications. *Eur Urol* 2009, 55, 1321-1330.

[51] D'Amico, A. V., Whittington, R., Malkowicz, S. B., Schultz, D., et al., Biochemical outcome after radical prostatectomy, external beam radiation therapy, or interstitial radiation therapy for clinically localized prostate cancer. *JAMA* 1998, 280, 969-974.

[52] Reis, S. T., Pontes-Junior, J., Antunes, A. A., Sousa-Canavez, J. M., et al., Tgf-beta1 expression as a biomarker of poor prognosis in prostate cancer. *Clinics (Sao Paulo)* 2011, 66, 1143-1147.

[53] Ricote, M., Garcia-Tunon, I., Bethencourt, F. R., Fraile, B., et al., Interleukin-1 (IL-1alpha and IL-1beta) and its receptors (IL-1RI, IL-1R11, and IL-1Ra) in prostate carcinoma. *Cancer* 2004, 100, 1388-1396.

[54] van Golen, K. L., Ying, C., Sequeira, L., Dubyk, C. W., et al., CCL2 induces prostate cancer transendothelial cell migration via activation of the small GTPase Rac. *J Cell Biochem* 2008, 104, 1587-1597.

[55] Jorgensen, T., Berner, A., Kaalhus, O., Tveter, K. J., et al., Up-regulation of the oligosaccharide sialyl LewisX: a new prognostic parameter in metastatic prostate cancer. *Cancer Res* 1995, 55, 1817-1819.

[56] Hong, Q., Sze, C. I., Lin, S. R., Lee, M. H., et al., Complement C1q activates tumor suppressor WWOX to induce apoptosis in prostate cancer cells. *PLoS One* 2009, 4, e5755.

---

The invention claimed is:

1. A method for diagnosing and treating prostate cancer in an individual comprising the steps of:
   a) providing a plasma sample to be tested from the individual;
   b) measuring the expression in the plasma sample of the biomarkers IL-4, IL-12, IL-9 and IL-1a and
   c) diagnosing the individual with prostate cancer when upregulated expression of IL-4, IL-12, IL-9 and IL-1a is detected; and
   d) treating the individual with prostate cancer by surgical removal of cancer cells, radiotherapy and/or chemotherapy.

2. The method according to claim 1 further comprising: providing one or more control plasma samples from an individual not afflicted with prostate cancer; and measuring the expression in the control plasma samples of the biomarkers measured in step (b); wherein the individual is diagnosed with prostate cancer when the expression in the test plasma sample of the biomarkers measured in step (b) is lower than the expression in the control plasma samples of the biomarkers measured in step (d).

3. The method according to claim 1, wherein step (b) comprises measuring the expression of one or more of the biomarkers listed in Table 1 (B), wherein at least 2, 3, 4, 5 or 6 of the biomarkers listed in Table 1 (B) are measured.

4. The method according to claim 1 wherein step (b) comprises measuring the expression of one or more biomarkers from the biomarkers listed in Table 1 (C), wherein at least 2, 3, 4, 5, 6, 7 or 8 of the biomarkers listed in Table 1 (C) are measured.

5. The method according to claim 1 wherein step (b) comprises measuring the expression of one or more biomarkers from the biomarkers listed in Table 1 (D), wherein at least 2, 3, 4, 5, 6, 7, 8, 9, 10 or 11 of the biomarkers listed in Table 1 (D) are measured.

6. The method according to claim 1, wherein step (b) comprises measuring the expression of all of the biomarkers listed in Table 1 (D).

7. The method according to claim 1 wherein step (b) comprises measuring the expression of one or more biomarkers from the biomarkers listed in Table 1 (E), wherein at least 2, 3, 4, 5, 6, 7 or 8 of the biomarkers listed in Table 1 (E) are detected.

8. The method according to claim 1 wherein step (b) comprises measuring the expression of one or more biomarkers from the biomarkers listed in Table 1 (F), wherein at least 2, 3, 4, 5, 6, 7 or 8 of the biomarkers listed in Table 1 (F) are detected.

9. The method according to claim 1 wherein step (b) comprises measuring the expression of one or more biomarkers from the biomarkers listed in Table 1 (G), for example at least 2, 3, 4, 5, 6, 7 or 8 of the biomarkers listed in Table 1 (G).

10. The method according to claim 1, wherein step (b) comprises measuring the expression of one or more biomarkers from the biomarkers listed in Table 1 (H), wherein at least 2, 3, 4 or 5 of the biomarkers listed in Table 1 (H) are measured.

11. The method according to claim 1 wherein step (b) comprises measuring the expression of one or more biomarkers from the biomarkers listed in Table 1 (I), wherein at least 2, 3, 4, 5, 6, 7, 8 or 9 of the biomarkers listed in Table 1 (I) are measured.

12. The method according to claim 1, wherein the method is for differentiating between risk group A (low risk), risk group B (moderate risk), risk group C (increased risk), risk subgroup C1 (moderately increased risk), risk subgroup C2 (importantly increased risk) and risk group D (high risk).

13. The method according to claim 2, wherein the individual not afflicted with prostate cancer is not afflicted with any other prostate-related disorder.

14. The method according to claim 1, wherein step (b) is performed using a first binding agent capable of binding to one or more biomarkers.

15. The method according to claim 1 wherein all of the biomarkers defined in Table 1 are used as prognostic and/or diagnostic markers.

16. The method according to claim 1, wherein step (b) further comprises measuring the expression of one or more of the biomarkers listed in Table 1 (B), wherein at least 2, 3, 4, 5 or 6 of the biomarkers listed in Table 1 (B) are measured.

17. The method according to claim 1 wherein step (b) further comprises measuring the expression of one or more biomarkers from the biomarkers listed in Table 1 (C), wherein at least 2, 3, 4, 5, 6, 7 or 8 of the biomarkers listed in Table 1 (C) are measured.

18. The method according to claim 1, further comprising measuring the expression of one or more biomarkers from the biomarkers listed in Table 1 (D), wherein at least 2, 3, 4, 5, 6, 7, 8, 9, 10 or 11 of the biomarkers listed in Table 1 (D) are measured.

19. The method according to claim 1, further comprising measuring the expression of all of the biomarkers listed in Table 1 (D).

20. The method according to claim 1 further comprising measuring the expression of one or more biomarkers from the biomarkers listed in Table 1 (E), wherein at least 2, 3, 4, 5, 6, 7 or 8 of the biomarkers listed in Table 1 (E) are detected.

21. The method according to claim 1 further comprising measuring the expression of one or more biomarkers from the biomarkers listed in Table 1 (F), wherein at least 2, 3, 4, 5, 6, 7 or 8 of the biomarkers listed in Table 1 (F) are detected.

22. The method according to claim 1 further comprising measuring the expression of one or more biomarkers from the biomarkers listed in Table 1 (G), for example at least 2, 3, 4, 5, 6, 7 or 8 of the biomarkers listed in Table 1 (G).

23. The method according to claim 1, comprising measuring the expression of one or more biomarkers from the biomarkers listed in Table 1 (H), wherein at least 2, 3, 4 or 5 of the biomarkers listed in Table 1 (H) are measured.

24. The method according to claim 1 further comprising measuring the expression of one or more biomarkers from the biomarkers listed in Table 1 (I), wherein at least 2, 3, 4, 5, 6, 7, 8 or 9 of the biomarkers listed in Table 1 (I) are measured.

25. The method according to claim 1 further comprising measuring all of biomarkers defined in Table 1.

* * * * *